United States Patent [19]
Ito et al.

[11] Patent Number: 5,717,485
[45] Date of Patent: Feb. 10, 1998

[54] FOREIGN SUBSTANCE INSPECTION APPARATUS

[75] Inventors: Masami Ito; Kenji Takamoto; Kanji Nishii; Tatsuo Nagasaki; Ken Shimono, all of Osaka, Japan

[73] Assignee: Matsushita Electric Industrial Co., Ltd., Japan

[21] Appl. No.: 637,230

[22] Filed: Apr. 24, 1996

[30] Foreign Application Priority Data

Apr. 24, 1995 [JP] Japan .................. 7-098547

[51] Int. Cl.[6] .................................. G01N 21/00
[52] U.S. Cl. .................................. 356/237; 356/369
[58] Field of Search .................. 356/365, 237; 250/225, 559.49

[56] References Cited

U.S. PATENT DOCUMENTS

| | | | |
|---|---|---|---|
| Re. 33,991 | 7/1992 | Shiba et al. | |
| 4,342,515 | 8/1982 | Akiba et al. | 356/237 |
| 4,669,875 | 6/1987 | Shiba et al. | |
| 4,965,454 | 10/1990 | Yamauchi et al. | |
| 5,046,847 | 9/1991 | Nakata et al. | |
| 5,225,886 | 7/1993 | Koizumi et al. | |
| 5,331,396 | 7/1994 | Yukawa et al. | 350/237 |
| 5,410,400 | 4/1995 | Shishido et al. | 356/237 |
| 5,424,536 | 6/1995 | Moriya | 250/225 |

OTHER PUBLICATIONS

Koizumi, et al., "Contaminant Detection Method Utilizing Polarization Characteristics of Light Reflected from LSI Patterns", *LSI*, vol. 25, No. 9, pp. 30–37, 1989 (no month available).

*Primary Examiner*—Frank G. Font
*Assistant Examiner*—Zandra V. Smith
*Attorney, Agent, or Firm*—Merchant, Gould, Smith, Edell, Welter & Schmidt, P.A.

[57] ABSTRACT

A foreign substance inspection apparatus having a good signal to noise ratio with optical detection accuracy capable of detecting infinitesimal foreign substances, comprising a lighting portion to irradiate with an S polarized laser light beam and having the optical axis parallel to the substrate to be inspected, a detecting portion having an optical axis located in a position set by rotating the optical axis of the lighting portion by 120° to 160° with the point of intersection of the optical axis of the lighting portion and the surface to be inspected as the center of rotation so as to have an angle made with the surface to be inspected of 45° or smaller to detect the area irradiated from the lighting portion by detecting the S polarized component in the scattered component from the foreign substances existing on the surface to be inspected and converting the S polarized component photoelectrically to a signal, and a signal processing portion to detect a foreign substance based on the signal outputted from the detecting portion.

30 Claims, 17 Drawing Sheets

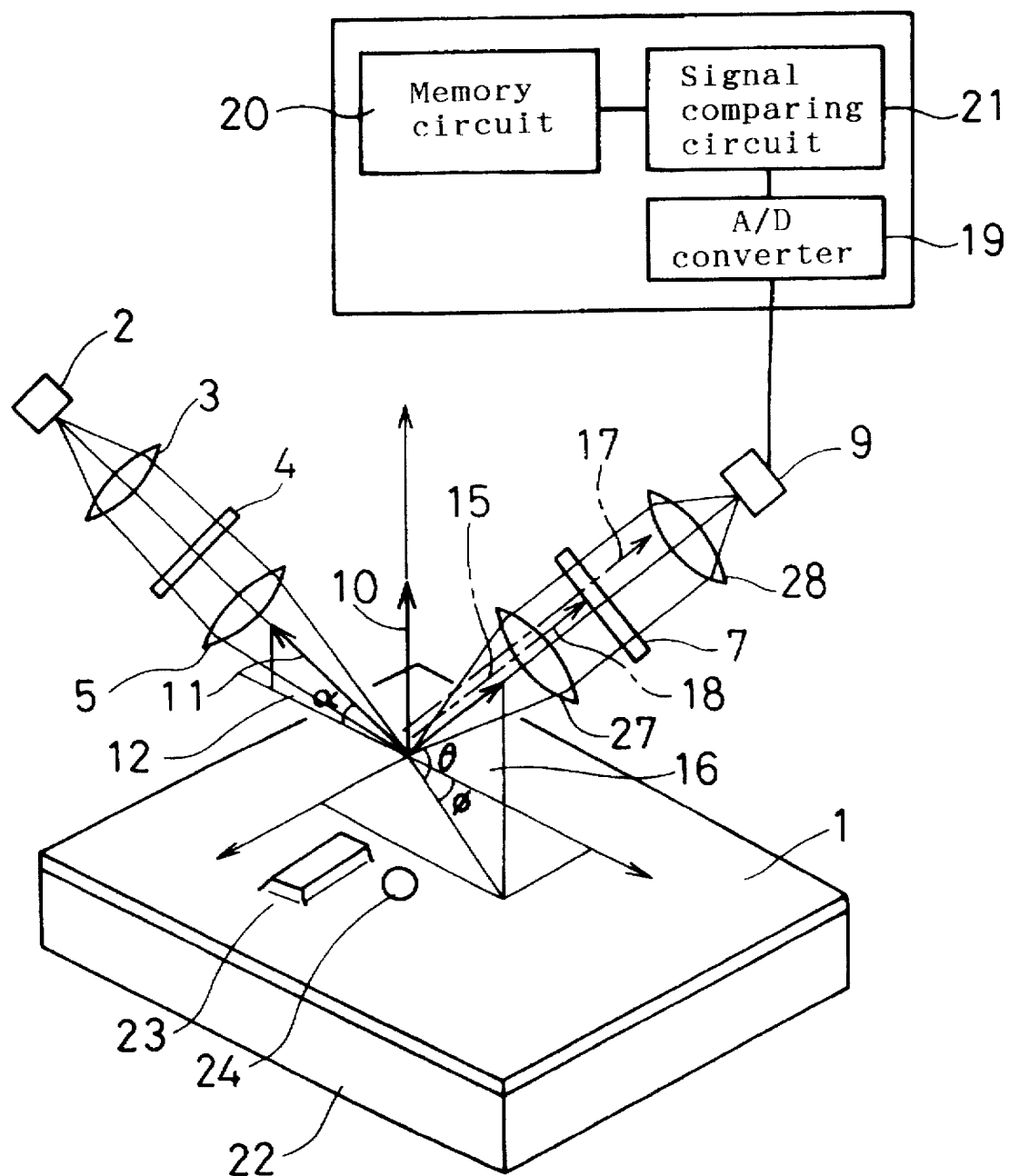
F I G. 8

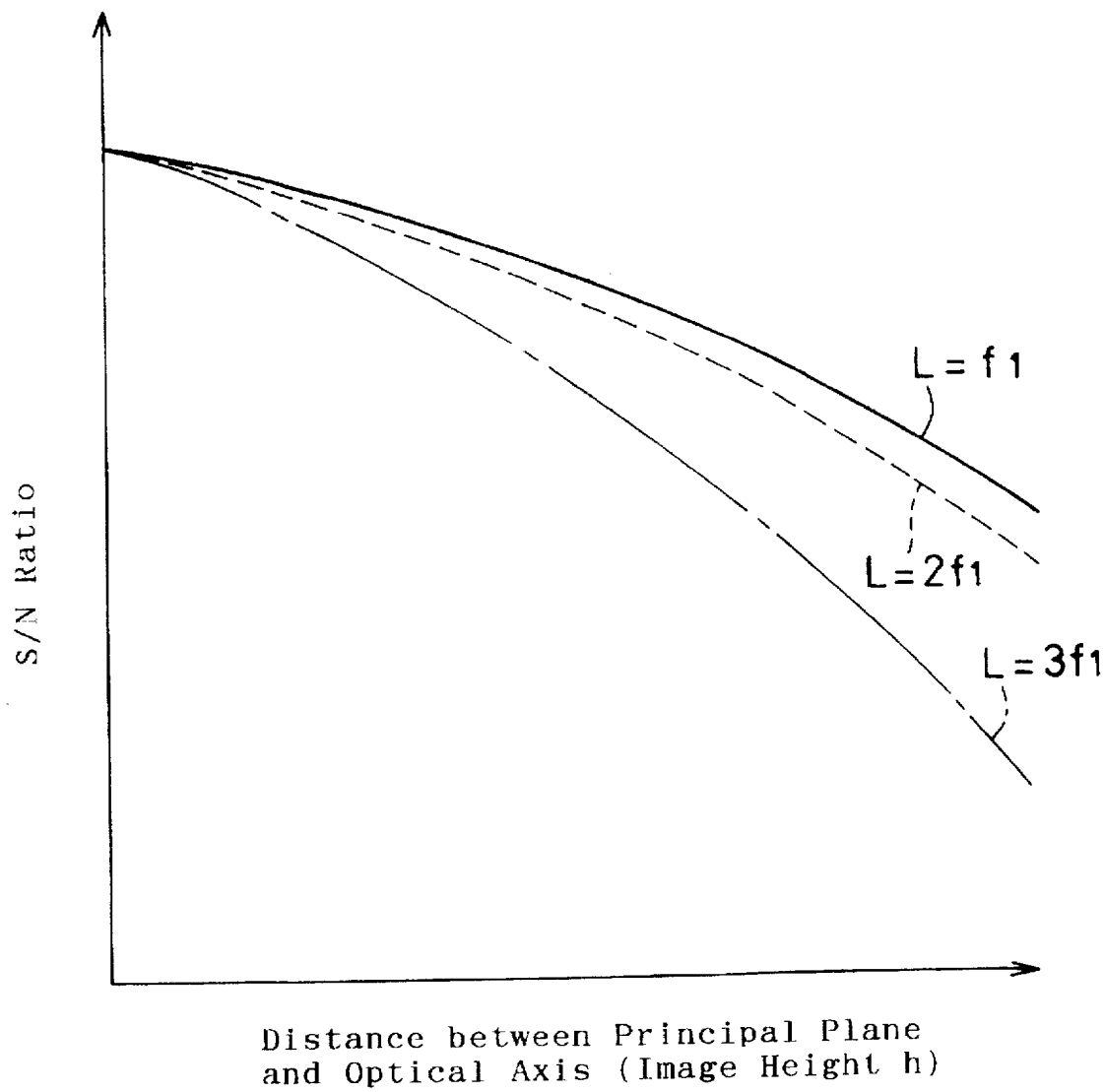
F I G. 10

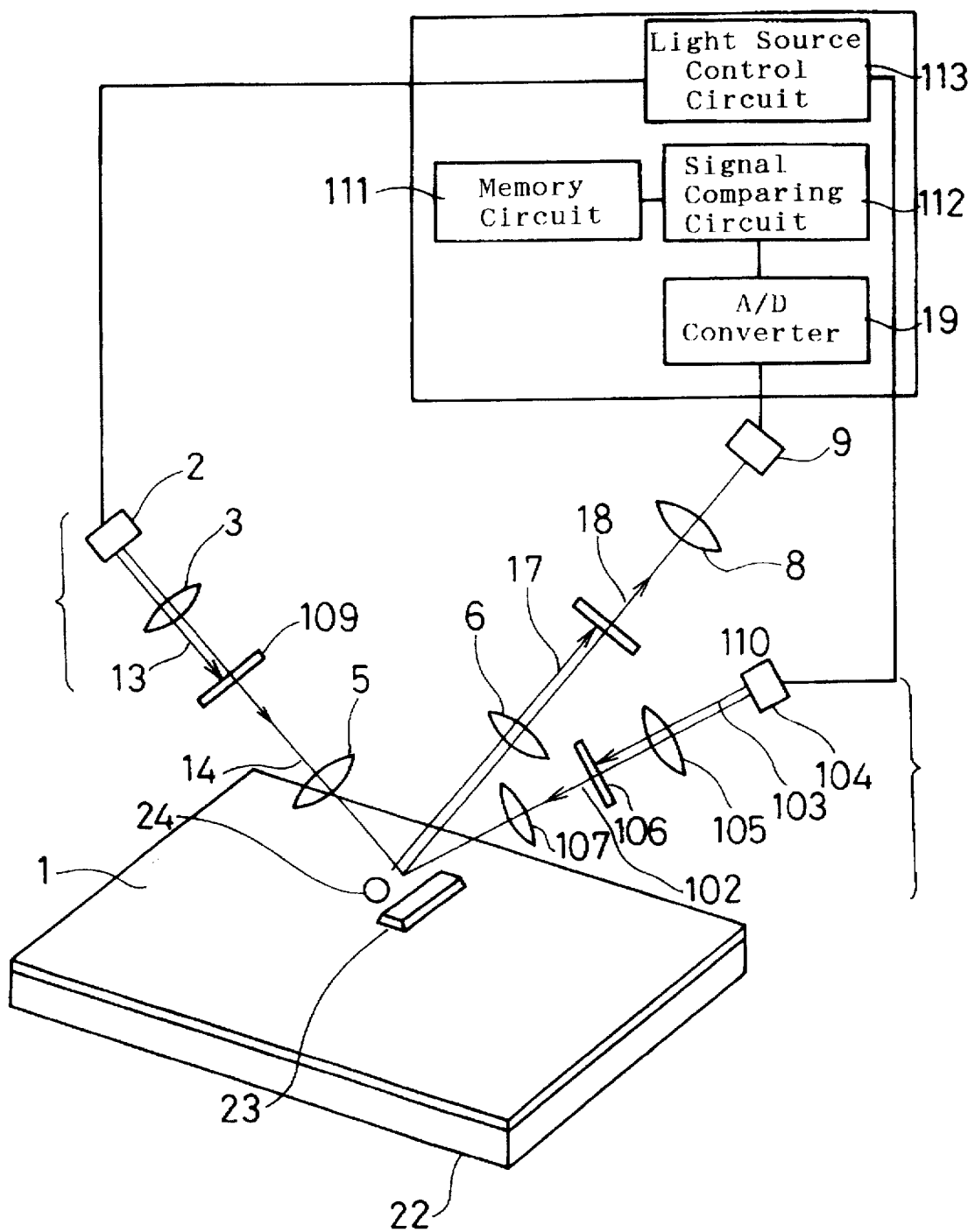
F I G. 12

FOREIGN SUBSTANCE INSPECTION APPARATUS

BACKGROUND OF THE INVENTION

1. Field of the Invention

The present invention relates to a foreign substance inspection apparatus for detecting foreign substances existing on an object surface, in particular, to a foreign substance inspection apparatus used for appearance inspection of substrates having a pattern during a liquid crystal production process or a semiconductor production process.

2. Description of the Prior Art

As an example, a basic structure of a conventional foreign substance inspection apparatus described in "Transactions of the Society of Instrument and Control Engineers" (vol. 25, No. 9,954/961, 1989) is illustrated in FIG. 17. Herein the plane including a surface 201a of a substrate 201 which is to be inspected and perpendicular to the surface of the paper sheet is defined to be the principal plane. In FIG. 17, a moving apparatus 204 can move parallel to the principal plane of the substrate 201. The substrate 201 is mounted on the moving apparatus 204. A pattern 202 on the substrate 201 is formed to make a 45° angle with respect to the principal plane of the substrate 201. An S polarized laser light source 205 ("S polarization" here denotes a polarization in a direction perpendicular to the surface of the paper sheet) is located so as to irradiate an S polarized laser light beam which is directed substantially parallel to the principal plane of the substrate 201. An objective lens 206, an analyzer 207 which transmits a P polarized light beam ("P polarization" here denotes a polarization in a direction parallel to the surface of the paper sheet), an image formation lens 208 and a photoelectric conversion element 209 are arranged so as to have an L axis as an optical axis perpendicular to the principal plane of the substrate 201.

Operation of a conventional foreign substance inspection apparatus with the above mentioned structure will be explained. When a light beam is irradiated from the S polarized light source 205 to the substrate 201 in a direction substantially parallel to the substrate 201, a reflected light beam 210 is reflected without disturbing polarization with the pattern 202. That is, the reflected S polarized light beam 210 transmits the objective lens 206 and then is shielded by the analyzer 207 preset to transmit a P polarized light beam but shield an S polarized light beam. When a foreign substance 203 exists on the substrate 201 to be inspected, by irradiating a light beam from the S polarized laser light source 205 to the foreign substance 203, scattering occurs by the foreign substance 203 to disturb the polarized component to provide a scattered light beam 211 including a P polarized component. The scattered light beam 211 transmits the objective lens 206, and then is shielded by the analyzer 207 to shield the S polarized component and to transmit only the P polarized component. The light beam transmitted through the analyzer 207 is focused on the photoelectric conversion element 209 by the image formation lens 208. By signals outputted from the photoelectric conversion element 209, the position of the foreign substance 203 can be detected.

However, with the above mentioned structure, although the P polarized component of the reflected light beam 210 from the pattern 202 becomes nil on the optical axis of the objective lens 206, a P polarized component is included in a reflected light beam having an angle with respect to the optical axis L, which becomes a source of a noise. In FIG. 17, with the premise that the angle made by a light beam from the laser light source 205 and the optical axis L of the objective lens 206 is a detecting angle θ, the relationship of the detecting angle θ and the light intensity of the P polarized component of the scattered light beam 211 from the foreign substance 203 which is detected by the photoelectric conversion element 209 are shown in FIG. 18. As apparent from FIG. 18, when the detecting angle θ is determined to be 90° in the prior art, the light intensity of the P polarized component of the scattered light beam 211 from the foreign substance 203 becomes weak. Accordingly, since the noise increases and the signal strength from the foreign substance becomes weak, the detection accuracy of the optical system deteriorates resulting in inability to detect infinitesimal foreign substances.

SUMMARY OF THE INVENTION

The present invention solves the above mentioned conventional problems. Namely, a purpose of the present invention is to provide a foreign substance inspection apparatus capable of detecting infinitesimal foreign substances with a good signal to noise ratio to obtain an optical detection accuracy.

In order to achieve the above mentioned object, a foreign substance inspection apparatus of the present invention comprises a lighting portion located so as to have an optical axis parallel to a surface of an object to be inspected, irradiating with an S polarized light beam with respect to the surface, and a detecting portion having an optical axis located in a position set by rotating the optical axis of the lighting portion by 120° to 160° with a point of intersection of the optical axis of the lighting portion and the surface of the object as the center of rotation so as to have an angle made with the surface to be inspected of 45° or smaller, in order to detect the area to which the light beam is irradiated by the lighting portion by detecting an S polarized component in a scattered component from foreign substances existing on the surface to be inspected and converting the S polarized component photoelectrically.

In the above mentioned configuration, it is preferable that the lighting portion comprises a laser light source, a collimator lens to convert light beams from the laser light source to parallel light beams, a polarizer and a cylindrical lens to focus the parallel light beams linearly having the back focal plane at the surface to be inspected. The detecting portion comprises an objective lens having the front focal plane at the back focal plane of the cylindrical lens, an analyzer, an image formation lens and a line sensor located at the focal plane of the image formation lens.

In the above mentioned aspect, it is preferable that an analog to digital conversion circuit to convert an analog signal outputted from the line sensor to a digital signal, a memory circuit to store a predetermined threshold to detect foreign substances, and a signal processing portion including a signal comparing circuit to compare the signals outputted from the analog to digital conversion circuit and the threshold stored in the memory circuit to detect the existence of foreign substances.

Another configuration of the foreign substance inspection apparatus of the present invention comprises a first lighting portion located so as to have an optical axis parallel to the surface of an object to be inspected, irradiating with a P polarized light beam with respect to the surface of the object to be inspected; a second lighting portion having an optical axis located in a position set by rotating the optical axis of the first lighting portion by 90° or larger with a point of intersection of the optical axis of the first lighting portion and the surface of the object as the center of rotation, irradiating with an S polarized light beam with respect to the surface of the object; a detecting portion to detect an area to which the light beams are irradiated from the first lighting portion and the second lighting portion by successively detecting a P polarized component in the front scattered component generated from a foreign substance existing on the surface of the object by the first lighting portion and a P polarized component in the back scattered component generated from the foreign substance existing on the surface to be inspected by the second lighting portion and converting the P polarized components photoelectrically, having an optical axis located in a position set by rotating the optical axis of the first lighting portion by 120° to 160° with the point of intersection of the optical axis of the first lighting portion and the surface to be inspected as the center of rotation so as to have an angle made with the surface to be inspected of 45° or smaller; and a signal processing portion to detect foreign substances based on signals outputted from the detecting portion and to classify light transmissivities of the foreign substances by comparing intensities of the front scattered component and the back scattered component.

In the above mentioned configuration, it is preferable that the first lighting portion comprises a first laser light source, a first collimator lens to convert light beams from the first laser light source to parallel light beams, a first polarizer and a first cylindrical lens to focus the parallel light beams linearly, having the back focal plane at the surface to be inspected. The second lighting portion comprises a second laser light source, a second collimator lens to convert light beams from the second laser light source to parallel light beams, a second polarizer and a second cylindrical lens to focus the parallel light beams linearly, having the back focal plane at the surface to be inspected. The detecting portion comprises an objective lens having a front focal plano at the back focal planes of the first and second cylindrical lenses, an analyzer, an image formation lens and a line sensor located at the focal plane of the image formation lens. The signal processing portion comprises an analog to digital conversion circuit to convert analog signals outputted from the line sensor to digital signals, a memory circuit to store foreign substance detection thresholds and foreign substance classification thresholds preset for foreign substance inspection, a signal comparing circuit for foreign substance judgment by comparing the signals outputted from the analog to digital conversion circuit and the thresholds stored in the memory circuit and a light source controlling circuit to control switching and intensity of the first and second laser light sources.

In the above mentioned configuration, it is preferable that the first lighting portion and the second lighting portion are set to irradiate the same area of the surface of the object to be inspected and the detecting portion detects images of the area.

In the above mentioned configuration, it is preferable that the first lighting portion includes a first polarizer oriented to transmit only the P polarized component of the light beam irradiated from the first lighting portion, the second lighting portion includes the second polarizer oriented to transmit only the S polarized component of the light beam irradiated from the second lighting portion, and the detecting portion includes the analyzer set to transmit only the P polarized component of the light beam entering the detecting portion.

Still another configuration of the foreign substance inspection apparatus of the present invention comprises a first lighting portion located so as to have an optical axis parallel to the surface of an object to be inspected and irradiating with a P polarized light beam with respect to the surface; a second lighting portion having an optical axis located in a position set by rotating the optical axis of the first lighting portion by 90° or larger with a point of intersection of the optical axis of the first lighting portion and the surface to be inspected as the center of rotation, irradiating with an S polarized light beam with respect to the surface having a wavelength different from that of the first lighting portion; a detecting portion to separate a P polarized component from the front scattered component which is generated by scattering the light beam from the first lighting portion and to separate a P polarized component from the back scattered component which is generated by scattering the light beam from the second lighting portion by a wavelength separating device, to detect the P polarized components simultaneously to be converted photoelectrically, having an optical axis located in a position set by rotating the optical axis of the first lighting portion by 120° to 160° at the point of intersection of the optical axis of the first lighting portion and the surface to be inspected as the center of rotation so as to have an angle made with the surface to be inspected of 45°; and a signal processing portion to detect foreign substances based on signals outputted from the detecting portion and to classify light transmissivities of the foreign substances by comparing intensities of the front scattered component and the back scattered component.

In the above mentioned configuration, it is preferable that the first lighting portion comprises a first laser light source to emit a laser light beam having a wavelength of $\lambda 1$, a first collimator lens to convert light beams from the first laser light source to parallel light beams, a first polarizer and a first cylindrical lens to focus the parallel light beams linearly, having a back focal plane at the surface of the substrate to be inspected. The second lighting portion comprises a second laser light source to emit a laser light beam having a wavelength of $\lambda 2$, a second collimator lens to convert light beams from the second laser light source to parallel light beams, a second polarizer and a second cylindrical lens to focus the parallel light beams linearly, having a back focal plane at the surface of the substrate to be inspected. The detecting portion comprises an objective lens having the front focal planes at the back focal plane of the first and second cylindrical lenses, a dichroic mirror to transmit a laser light having wavelength of $\lambda 1$ and to reflect laser light having a wavelength of $\lambda 2$, an analyzer oriented so as to transmit only the P polarized component of $\lambda 1$ and $\lambda 2$ in the detection plane, an image formation lens to focus images in the surface to be inspected on a line sensor, a first line sensor to detect a wavelength of $\lambda 1$, and a second line sensor to detect a wavelength of $\lambda 2$. The signal processing portion comprises an analog to digital conversion circuit to convert analog signals detected by the first line sensor and the second line sensor to digital signals, a memory circuit to store foreign substance detection thresholds and foreign substance classification thresholds preset for foreign substance inspection, and a signal comparing circuit for foreign substance judgment by comparing the signals outputted from the analog to digital conversion circuit and the thresholds stored in the memory circuit.

In the above mentioned configurations, it is preferable that a spatial filter to eliminate a cyclic pattern of the object to be inspected is further comprised.

In the above mentioned configurations, it is preferable that the spatial filter is located between the objective lens and the image formation lens of the detecting portion.

In the above mentioned configurations, it is preferable that the spatial filter is prepared by making and recording a Fourier transform image of cyclic pattern data of the surface to be inspected of the object to be inspected on a photographic plate so as to block the cyclic pattern.

In the above mentioned configurations, it is preferable that the spatial filter is prepared by irradiating a cyclic pattern of the surface of the object to be inspected and recording reflected light on a photographic plate located at a predetermined position behind the objective lens so as to block the cyclic pattern.

Alternatively, in the above mentioned configurations, it is preferable that a signal processing means to eliminate a cyclic pattern of the object to be inspected from the electrical signals outputted from the detecting portion is further comprised.

In the above mentioned configurations, it is preferable that the signal processing portion further comprises a cyclic pattern eliminating circuit to cut a cyclic pattern noise.

Furthermore, in the above mentioned configurations, it is preferable that the detecting portion comprises at least an optical system including an objective lens having a focal length of f and an aperture diameter of D1, and an image formation lens having the principal plane with a distance L from the principal plane of the objective lens preset to have the aperture diameter D2 satisfying the below mentioned formula:

$$D2 \geq D1 - 2A + (AL/f) \quad (1)$$

wherein A denotes the width of the area to be inspected.

In the above mentioned aspects, it is preferable that the detecting portion includes a telecentric optical system.

According to the foreign substance inspection apparatus of the present invention having the above mentioned aspects, the lighting portion is located so as to have the optical axis parallel to the surface of the object to be inspected and irradiates with the S polarized light beam with respect to the surface. The detecting portion has the optical axis located in the position set by rotating the optical axis of the lighting portion by 120° to 160° with the point of intersection of the optical axis of the lighting portion and the surface to be inspected as the center of rotation so as to have the angle made with the surface to be inspected of 45° or smaller. Thus, the detecting portion detects the area to which the light beam is irradiated by the lighting portion by detecting the S polarized component in the scattered component from the foreign substances existing on the surface to be inspected and converts the S polarized component photoelectrically. The front scattered light beam can be detected with a signal strength to show the existence of foreign substances of several hundred times as much as that of conventional methods. On the other hand, since the light beam reflected from the surface to be inspected has a large tilt angle, it barely enters the detecting portion to enable reduction of a noise caused by a light beam reflected from the pattern on the surface to be inspected. As a consequence, existence of foreign substances can be detected with a high accuracy.

The lighting portion comprises the laser light source, the collimator lens to convert the light beams from the laser light source to the parallel light beams, the polarizer and the cylindrical lens to focus the parallel light beams linearly, having the back focal plane at the surface to be inspected. The detecting portion comprises the objective lens having the front focal plane at the back focal plane of the cylindrical lens, the analyzer, the image formation lens and the line sensor located at the focal plane of the image formation lens. Thus, the S polarized laser light beam can be generated and also the S polarized component can be detected separately with a simple structure.

The analog to digital conversion circuit converts the analog signal outputted from the line sensor to the digital signal. The memory circuit stores the predetermined threshold to detect foreign substances. The signal processing portion including a signal comparing circuit compares the signal outputted from the analog to digital conversion circuit and the threshold stored in the memory circuit to inspect foreign substances. Thus, existence of foreign substances can be judged.

According to another configuration of the foreign substance inspection apparatus of the present invention, the first lighting portion and the second lighting portion are switched on alternately and the signal processing portion compares a first outputted signal generated by the irradiation from the first lighting portion and detected with the detecting portion and a second outputted signal generated by the irradiation from the second lighting portion and detected with the detecting portion. Ratios of the P polarized component and the S polarized component in the outputted signals differ according to the kind of foreign substances existing on the surface to be inspected to enable not only the inspection of foreign substances but also the classification of foreign substances by comparing the front scattered component and the back scattered component of foreign substances.

The first lighting portion comprises the first laser light source, the first collimator lens to convert light beams from the first laser light source to parallel light beams, the first polarizer and the first cylindrical lens to focus the parallel light beams linearly, having the back focal plane at the surface to be inspected. The second lighting portion comprises the second laser light source, the second collimator lens to convert light beams from the second laser light source to parallel light beams, the second polarizer and the second cylindrical lens to focus the parallel light beams linearly having the back focal plane at the surface to be inspected. The detecting portion comprises the objective lens having the front focal plane at the back focal planes of the first and second cylindrical lenses, the analyzer, the image formation lens and the line sensor located at the focal plane of the image formation lens. The signal processing portion comprises the analog to digital conversion circuit to convert the analog signals outputted from the line sensor to the digital signals, the memory circuit to store foreign substance detection thresholds and foreign substance classification thresholds preset for foreign substance inspection, the signal comparing circuit for foreign substance judgment by comparing the signal outputted from the analog to digital conversion circuit and the thresholds stored in the memory circuit and the light source controlling circuit to control switching and intensity of the first and second laser light sources. Thus, a production cost of the apparatus can be reduced by having a common structure for the first lighting portion and the second lighting portion.

The first lighting portion and the second lighting portion are set to irradiate the same area of the surface of the object to be inspected. The detecting portion detects images of the area. An optical system of the first and second lighting portions can be minimal to achieve the downsizing of the apparatus.

The first lighting portion includes the first polarizer oriented to transmit only the P polarized component of a light beam irradiated from the first lighting portion. The second lighting portion includes the second polarizer oriented to transmit only the S polarized component of a light beam irradiated from the second lighting portion. The detecting portion includes the analyzer set to transmit only the P polarized component of a light beam entering the detecting portion. Thus, a noise generated by a light beam reflected from the pattern on the surface to be inspected can be reduced.

The further different aspect of the foreign substance inspection apparatus of the present invention has the first light beam having the wavelength of $\lambda 1$ of the first laser light source and the second light beam having the wavelength of $\lambda 2$, and the P polarized component in the front scattered component generated from the foreign substance existing on the surface to be inspected by the first lighting portion and the P polarized component in the back scattered component generated from the foreign substance existing on the surface to be inspected by the second lighting portion are separated by means of the wavelength separating device, and detected simultaneously to be converted photoelectrically. Thus, foreign substance inspection and foreign substance classification are enabled in a continuous foreign substance inspection operation.

The first lighting portion comprises the first laser light source to emit the laser light beam having the wavelength of $\lambda 1$, the first collimator lens to convert light beams from the first laser light source to parallel light beams, the first polarizer and the first cylindrical lens to focus the parallel light beams linearly, having the back focal plane at the surface to be inspected. The second lighting portion comprises the second laser light source to emit the laser light beam having the wavelength of $\lambda 2$, the second collimator lens to convert light beams from the second laser light source to parallel light beams, the second polarizer and the second cylindrical lens to focus the parallel light beams linearly, having the back focal plane at the surface to be inspected. The detecting portion comprises the objective lens having the front focal plane at the back focal planes of the first and second cylindrical lenses, the dichroic mirror to transmit the laser light having wavelength of $\lambda 1$ and to reflect the laser light having wavelength of $\lambda 2$, the analyzer oriented so as to transmit only the P polarized component of wavelengths $\lambda 1$ and $\lambda 2$ in the detection plane, the image formation lens to focus images in the surface to be inspected on the line sensor, the first line sensor to detect laser beam having wavelength of $\lambda 1$, and the second line sensor to detect laser light having wavelength of $\lambda 2$. The signal processing portion comprises the analog to digital conversion circuit to convert the analog signals detected by the first line sensor and the second line sensor to the digital signals, the memory circuit to store foreign substance detection thresholds and foreign substance classification thresholds preset for foreign substance inspection, and the signal comparing circuit for foreign substance judgment by comparing the signals outputted from the analog to digital conversion circuit and the thresholds stored in the memory circuit. Thus, the signal processing portion can be formed with a simple structure by having a common structure for main parts of the first lighting portion and the second lighting portion.

In the above mentioned configurations, since the spatial filter to eliminate the cyclic pattern of the object to be inspected is further comprised, the cyclic noise generated by a light beam reflected from an edge portion of a cyclic pattern on the surface of the object to be inspected can be eliminated.

In the above mentioned configurations, since the spatial filter is located between the objective lens and the image formation lens of the detecting portion, a short conjugate distance of an optical system of the detecting portion can be achieved.

In the above mentioned configurations, since the spatial filter is prepared by making and recording the Fourier transform image of the cyclic pattern datum of the surface to be inspected of the object to be inspected on the photographic plate so as to block the cyclic pattern, or by irradiating the cyclic pattern of the surface to be inspected of the object to be inspected and recording the reflected light on the photographic plate located at the predetermined position behind the objective lens so as to block the cyclic pattern, cycles of the spatial filter and the object to be inspected can be identical to prevent the generation of moire.

In the above mentioned configurations, since the signal processing means to eliminate the cyclic pattern of the object to be inspected from signals outputted from the detecting portion is further comprised, the cyclic noise generated by the light beam reflected from an edge portion of the cyclic pattern on the surface of the object to be inspected can be eliminated similarly.

In the above mentioned configurations, since the signal processing portion further comprises the cyclic pattern eliminating circuit to cut the cyclic pattern noise, the noise generated by the cyclic pattern can be eliminated easily without changing the structure of the lighting portion or the detecting portion.

In the above mentioned configurations, since the detecting portion comprises at least an optical system including the objective lens having the focal length of f and the aperture diameter of D1, and the image formation lens having the principal plane with the distance L from the principal plane of the objective lens preset to have the aperture diameter D2 satisfying the below mentioned formula:

$$D2 \geq D1 - 2A + (AL/f) \qquad (1)$$

wherein A denotes the width of the area to be inspected, the optical system having the aperture greater than that of the cofocal optical system outside the optical axis to receive a greater amount of light beam from foreign substances outside the optical axis as well. Therefore, foreign substances can be inspected with a high accuracy outside the optical axis.

In the above mentioned configurations, since the detecting portion includes the telecentric optical system, the magnification of the object to be inspected and the image thereof barely changes even when the surface of the substrate is not smooth. Therefore, foreign substances can be inspected with a high accuracy.

BRIEF DESCRIPTION OF THE DRAWINGS

FIG. 8 is a perspective view of a foreign substance inspection apparatus of a fourth embodiment of the present invention.

FIG. 10 is a graph illustrating a relationship between a length from the optical axis and a signal to noise ratio in the fourth embodiment.

FIG. 12 is a perspective view of a foreign substance inspection apparatus of a sixth embodiment of the present invention.

DETAILED DESCRIPTION OF THE INVENTION (First Embodiment)

Figure 1:
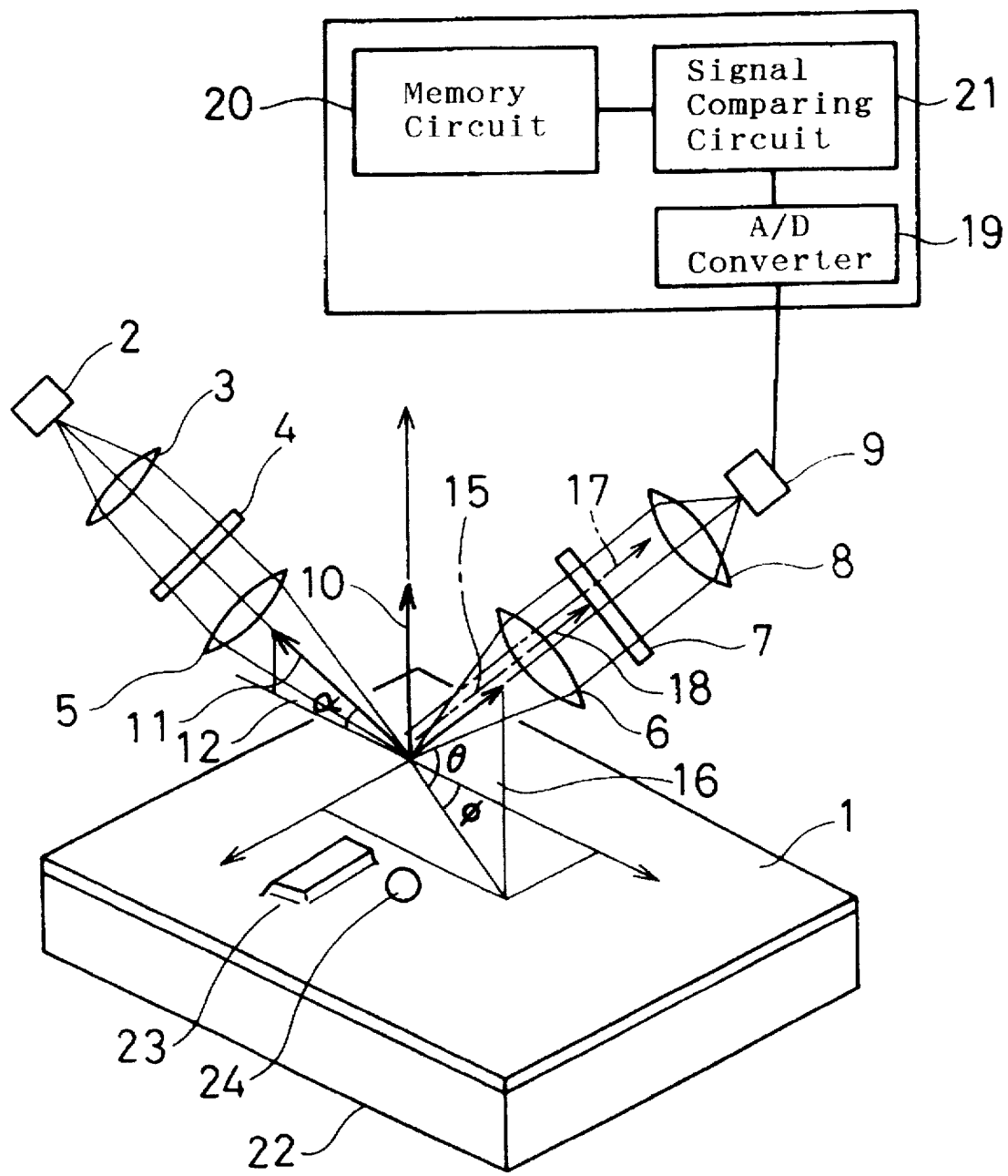
FIG. 1 is a perspective view of a foreign substance inspection apparatus of a first embodiment of the present invention.

A first embodiment of a foreign substance inspection apparatus of the present invention will be explained with reference to FIGS. 1 to 5. FIG. 1 is a perspective view of a foreign substance inspection apparatus of First Embodiment, and FIG. 2 is a diagram illustrating vectors of FIG. 1.

In FIG. 1, the foreign substance inspection apparatus of the first embodiment comprises a laser light source 2, a collimator lens 3 to convert light beams from the laser light source 2 into parallel light beams, a polarizer 4, a cylindrical lens 5 to focus the parallel light beams linearly, having the back focal plane at the surface of a substrate 1 which is to be inspected, an objective lens 6 having the front focal plane at the back focal plane of the cylindrical lens 5, an analyzer 7, an image formation lens 8, a line sensor 9 located at the focal plane of the image formation lens 8, an analog to digital conversion circuit (A/D converter) 19 for analog to digital conversion of signals outputted from the line sensor 9, a memory circuit 20 to store thresholds preset for foreign substance inspection, a signal comparing circuit 21 for foreign substance inspection by comparing the signals outputted from the analog to digital conversion circuit 19 and the thresholds stored in the memory circuit 20, and a XY moving base 22 to place and move two-dimensionally the substrate 1 to be inspected. Herein, the laser light source 2, the collimator lens 3, the polarizer 4 and the cylindrical lens 5 comprise the lighting portion. The objective lens 6, the analyzer 7, the image formation lens 8 and the line sensor 9 comprise the detecting portion. And the A/D converter 19, the memory circuit 20 and the signal comparing circuit 21 comprise the signal processing portion. Convex and concave patterns are cyclically provided on the surface of the object to be inspected. However, only one pattern 23 is schematically shown in the figures.

In FIG. 1, a normal vector 10 illustrates a vector perpendicular to the surface of the substrate 1 to be inspected, while an incident orientation vector 11 illustrates the optical axis of the optical system including the laser light source 2, the collimator lens 3 and the cylindrical lens 4. The angle determined by the incident orientation vector 11 and the substrate 1 is defined to be the angle of incidence $\alpha$, which is set to be 1° to 5°. Further, the incidence plane 12 is a plane determined by the normal vector 10 and the incident orientation vector 11.

Figure 2:
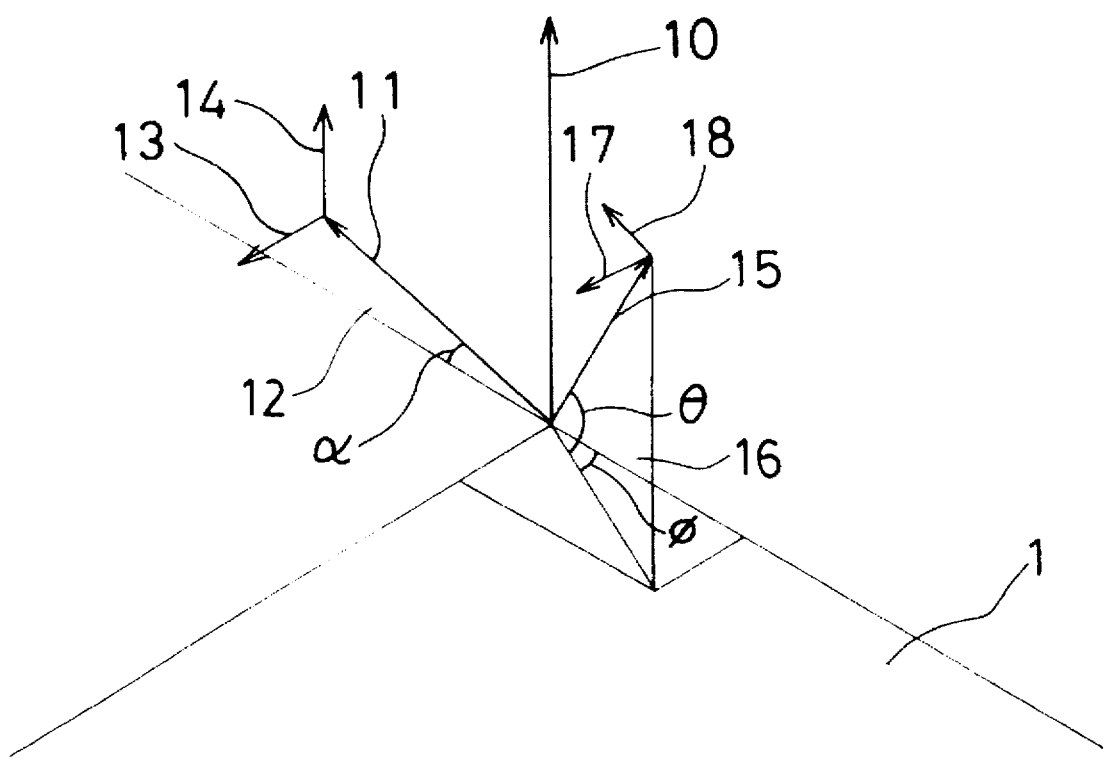
FIG. 2 is a diagram illustrating vectors in the first embodiment.

In FIG. 2, an S polarized laser light beam 13 has an electric vector component vibrating perpendicularly with respect to the incidence plane 12. A P polarized light beam 14 has an electric vector component vibrating in the incidence plane 12. The polarizer 4 is set to transmit only the S polarized laser light beam 13. A detection orientation vector 15 illustrates an optical axis of an optical system including the objective lens 6 and the image formation lens 8. The angle determined by the detection orientation vector 15 and the substrate 1 to be inspected is defined to be the detecting angle $\theta$, which is set to be 0° to 45°. Further an angle determined by the projected vectors of the incident orientation vector 11 or the detection orientation vector 15 is defined to be an angle of azimuth $\phi$, which is set to be 20° to 60°. The detection plane 16 is a plane including the normal vector 10 and the detection orientation vector 15.

In FIG. 2, an S polarized laser light beam 17 has an electric vector component vibrating perpendicularly with respect to the detection plane 16. A P polarized laser light beam 18 has an electric vector component vibrating in the detection plane 16. The analyzer 7 is set to transmit only the S polarized laser light beam 17.

Operation of the foreign substance inspection apparatus of the first embodiment will now be explained. A laser light beam from the laser light source 2 is converted to a parallel light beam by the collimator lens 3. Only an S polarized laser light beam 13 with respect to the incidence plane 12 is transmitted by the polarizer 4 to irradiate only the S polarized laser light beam 13 of the incidence plane 12 to an area of the surface of the substrate 1 linearly at a comparatively low angle of incidence $\alpha$, about 1° to 5° by means of the cylindrical lens 5. The S polarized laser light beam 13 in the incidence plane 12 is reflected by the pattern 23 on the surface of the substrate 1, or is scattered by the foreign substance 24 which exists on the substrate 1.

Figure 3:
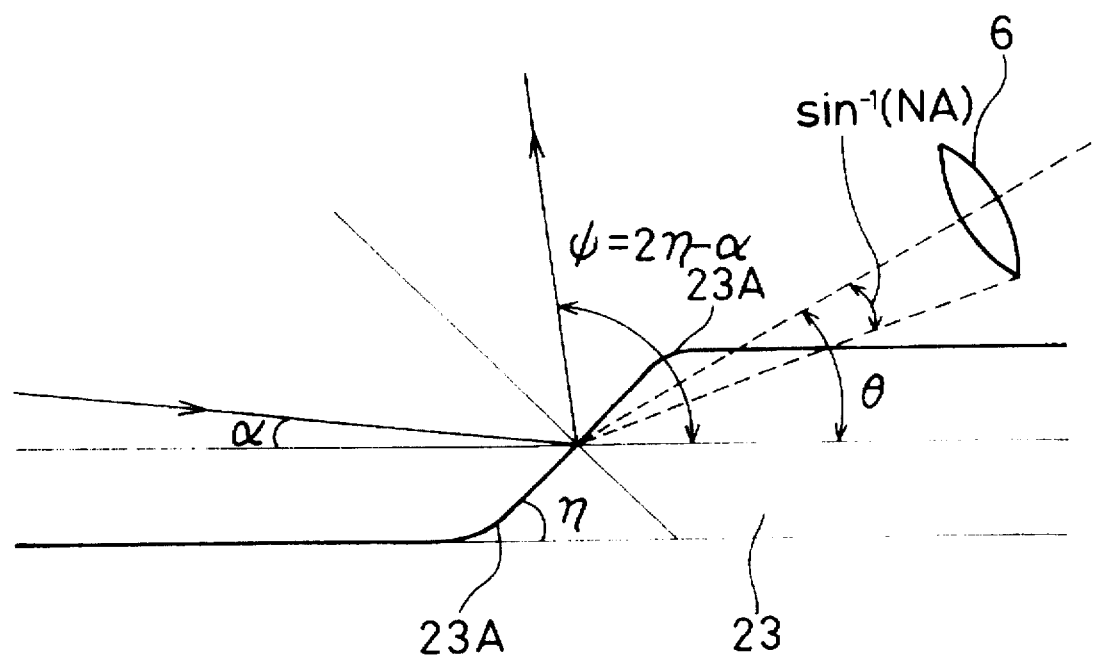
FIG. 3 is a side view illustrating a pattern of a reflected light beam in the first embodiment.

As apparent from FIG. 3, an angle $\phi$ (defined as the reflecting angle) determined by a laser light beam reflected by the pattern 23 on the substrate 1 and the substrate 1 can be found geometrically from the tilt angle $\eta$ of the pattern 23 and the angle of incidence $\alpha$ by the following formula:

$$\phi = 2\eta - \alpha. \tag{2}$$

The range of the reflecting angle $\phi$, which can enter the objective lens 6, can be found geometrically from the numerical aperture NA of the objective lens 6 and the detecting angle $\theta$ by the following formula:

$$\theta - \sin^{-1}(NA) \leq \phi \leq \theta + \sin^{-1}(NA) \tag{3}.$$

From the above mentioned formulae (2) and (3), the range of the tilt angle $\eta$ of the pattern 23, which can enter the objective lens 6 can be found by the following formula:

$$\{\theta - \sin^{-1}(NA) + \alpha\}/2 \leq \eta \leq \{\theta + \sin^{-1}(NA) + \alpha\}/2 \tag{4}.$$

In the above mentioned formula (4), with a detected angle of 45° and a numerical aperture (NA) of 0.3 for the objective lens 6, the range of the tilt angle $\eta$ of the pattern 23, which can enter the objective lens 6 is found to be $15° \leq \eta \leq 32°$ Since such a tilt angle barely exists even when a semiconductor device is produced with either a dry etching method or a wet etching method, a light beam reflected by the pattern 23 does not enter the objective lens 6. However, since a tilt angle is not in the above mentioned range at a minute curved portion 23A of the pattern 23 as shown in FIG. 3, a reflected light beam enters the objective lens 6 only from this portion. By having a detecting angle θ of 45° or smaller, the effect of a noise can be minimized.

Figure 4:
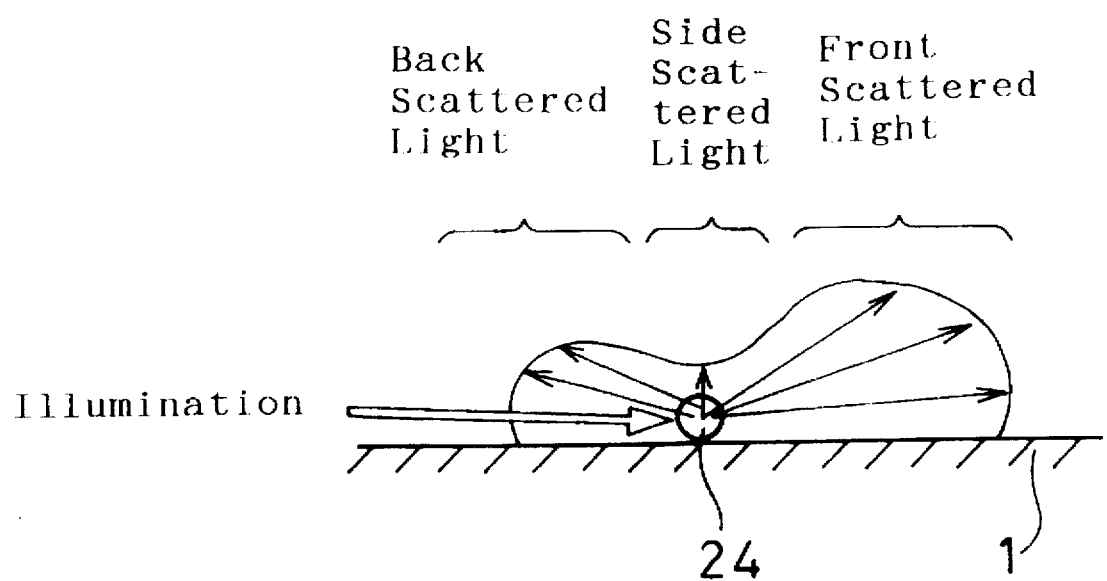
FIG. 4 is a diagram illustrating a scattered light intensity distribution caused by a foreign substance.
Figure 5:
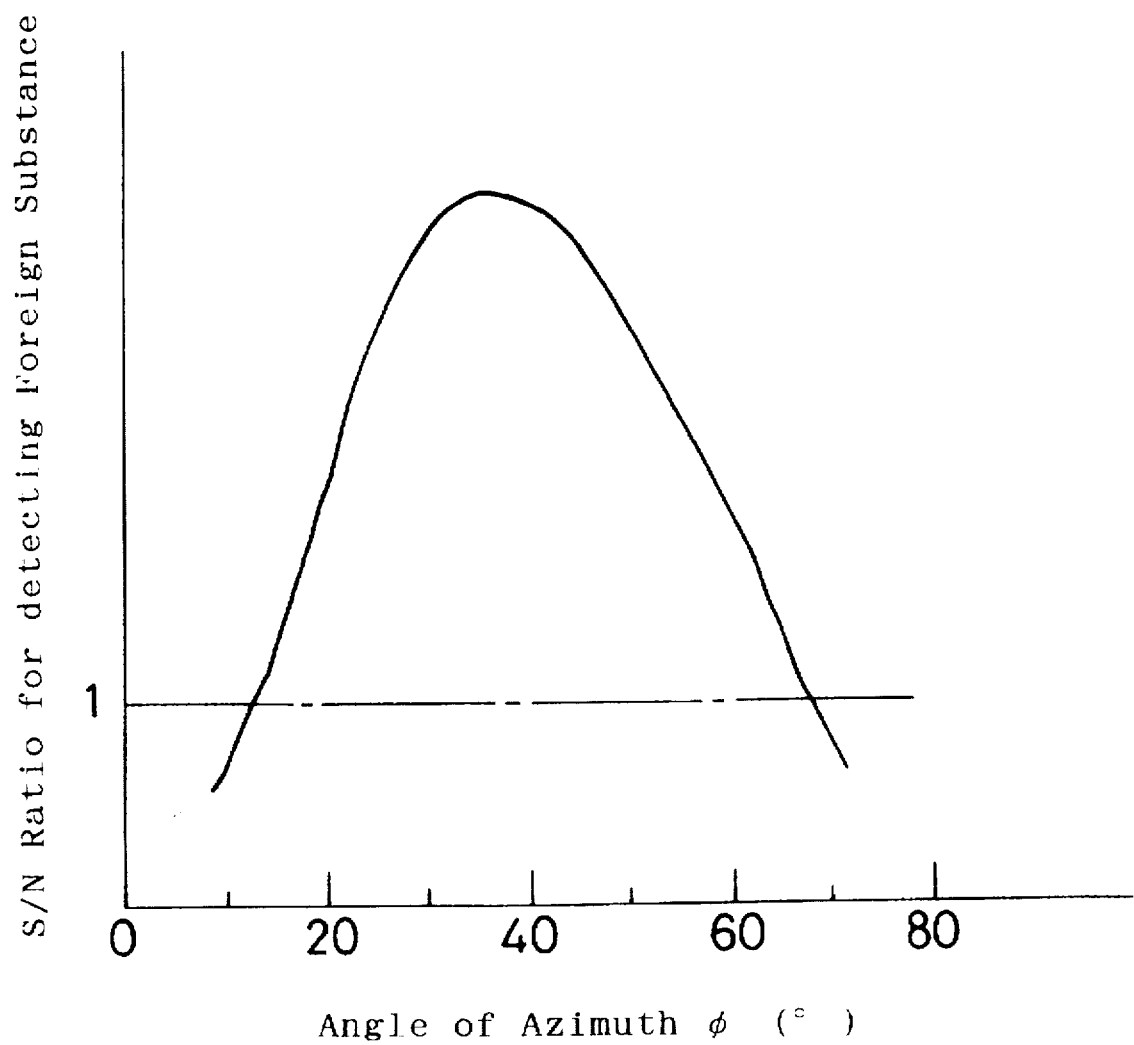
FIG. 5 is a graph illustrating a relationship between an angle of azimuth and a signal to noise ratio in the first embodiment.

On the other hand, a laser beam scattered by an infinitesimal foreign substance 24 has an intensity distribution illustrated in FIG. 4. Some of the front scattered light beam enters the aperture of the objective lens 6 of the detecting portion. The front scattered light beam has a strong absolute intensity as illustrated, and includes a high ratio of the S polarized laser light beam 17 with respect to the detection plane 16. Therefore a high signal intensity can be obtained compared with a case having the detection orientation vector 15 backward or sideward.

Accordingly, only the S polarized laser light beam 17 with respect to the detection plane 16 is transmitted by the analyzer 7 from a light beam incident to the objective lens 6 and focused on the line sensor 9 by the image formation lens 8. The S polarized laser light beam 17 with respect to the detection plane 16 is converted photoelectrically by the line sensor 9 and the detected signal is converted from analog to digital by the A/D converter 19. By comparing the detected signal converted from analog to digital and a threshold preset in the memory circuit 20 by the signal comparing circuit 21, existence of a foreign substance is judged. Then, by moving the specimen XY moving base 22, the foreign substance inspection on the entire surface of the substrate 1 to be inspected can be conducted.

The reason for using the S polarized laser light beam 13 as the incident polarized light beam and the S polarized light beam 17 as the detection polarized light beam will now be described. Table 1 shows the result of the experiment comparing a case of inspecting a foreign substance 24 with an S polarized laser light beam 13 in the incidence plane to an S polarized laser light beam 17 in the detection plane and a case of inspecting a foreign substance 24 with a P polarized laser light beam 14 in the incidence plane to a P polarized laser light beam 18 in the detection plane with an angle of incidence α of 2°, a detecting angle θ of 30°, and an angle of azimuth φ of 45°. The intensity of the irradiated light beam was the same.

TABLE 1

|  | A | B |
|---|---|---|
| Signal from a foreign substance | 63 | 21 |
| Noise from the pattern | 1 (Reference value) | 3 |
| Foreign substance detecting signal to noise ratio | 63 | 7 |

Note: In Table 1, A denotes the case of irradiating an S polarized laser light beam in the incidence plane and detecting the S polarized laser light beam in the detection plane, and B denotes the case of irradiating a P polarized laser light beam in the incidence plane and detecting the P polarized laser light beam in the detection plane.

As apparent from Table 1, in the case of conducting inspection by irradiating the substrate 1 with the S polarized laser light beam 13 in the incidence plane and detecting the S polarized laser light beam 17 in the detected plane, since the signal from the foreign substance 24 can be obtained with a high intensity and a noise from the pattern 23 is low, existence of the foreign substance 24 can be inspected with a high signal to noise ratio.

As heretofore mentioned, according to the first embodiment, since a lighting portion irradiates an S polarized laser light beam 13 linearly with an angle of incidence α in the range of 1° to 5° and a detecting portion to detect an S polarized laser light beam 17 with a detecting angle θ in the range of 0° to 45° and an angle of azimuth φ in the range of 20° to 60°, a front scattered light beam can be detected with a signal amount to show the existence of foreign substances of hundreds of times as much as that of conventional methods. On the other hand, owing to a large pattern tilt angle of 50° or larger, the light beam reflected from the pattern 23 barely enters the objective lens 6 which results in reduction of noise caused by the light reflected from the pattern 23. As a consequence, inspection of the foreign substance 24 can be conducted with a high accuracy.

Owing to a large signal amount from the foreign substance 24, a light source with a small power can be used to allow cost reduction. Further, since a signal to noise (S/N) ratio sufficient for the foreign substance detection can be ensured with a smaller numerical aperture (NA) of the objective lens 6 owing to the large signal amount from the foreign substance 24, the effect of defocus caused by surface roughness of the substrate 1 to be inspected can be eliminated by deepening the depth of focus of the detecting portion. Owing to a good foreign substance detecting S/N ratio, a predetermined signal to noise ratio can be ensured even with a low inspection magnification. Therefore, inspection can be conducted in a wide field of view with an enlarged field of view of the detecting portion.

(Second Embodiment)

Figure 6:
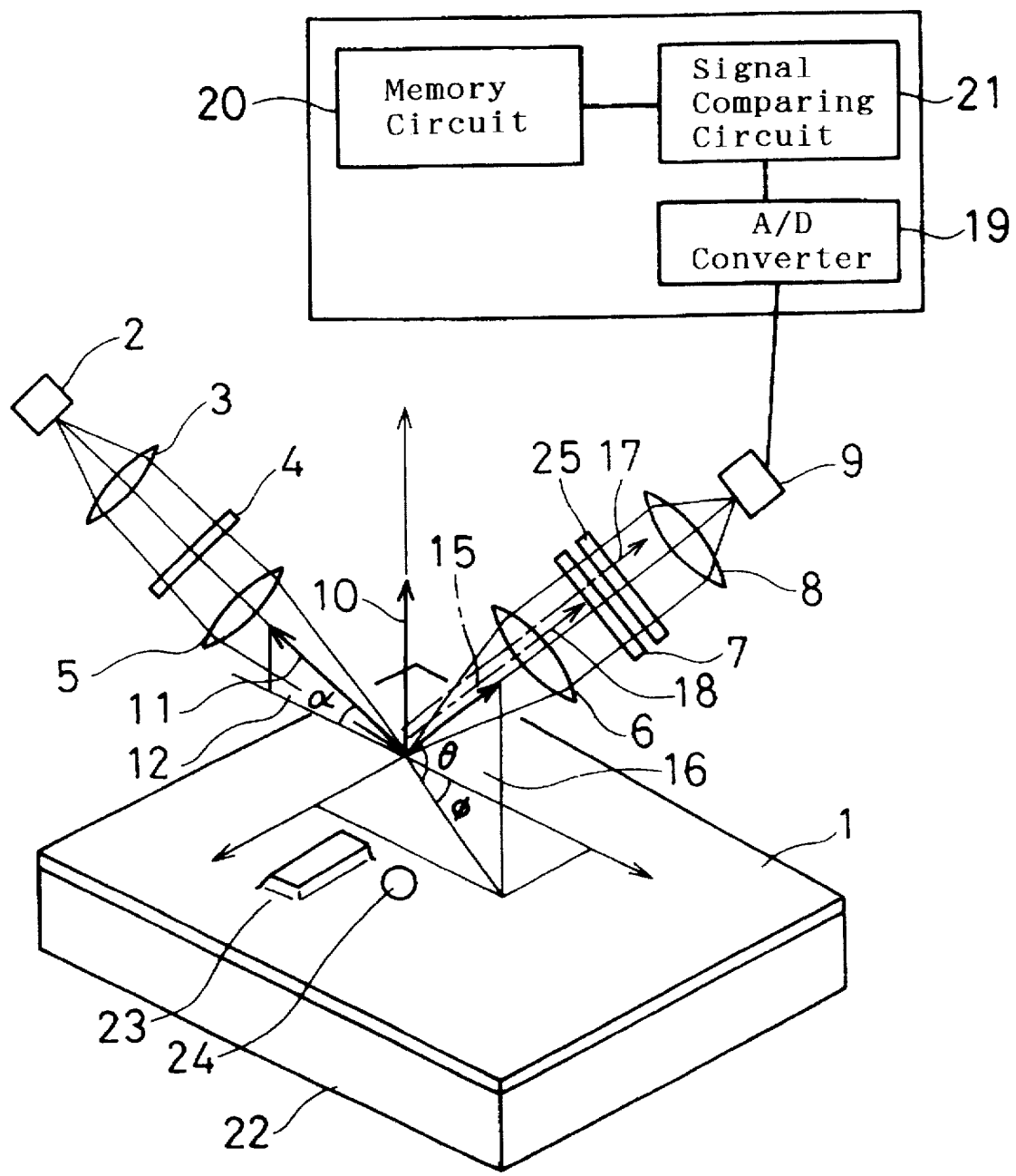
FIG. 6 is a perspective view of a foreign substance inspection apparatus of a second embodiment of the present invention.

A second embodiment of a foreign substance inspection apparatus of the present invention is illustrated in FIG. 6. Elements in FIGS. 1 and 6 bearing the same numerals are substantially the same. The apparatus of the second embodiment differs from the apparatus of the first embodiment in that the second embodiment further comprises a spatial filter 25 between the objective lens 6 and the image formation lens 8 to cut cyclic pattern noises.

The spatial filter 25 can be formed as follows. With CAD data of a cyclic pattern of the substrate 1 to be inspected, a Fourier transform image of the cyclic pattern is formed and recorded on a photographic plate so as to shield the cyclic pattern. Or a cyclic pattern of the substrate 1 is irradiated to a photographic plate located at a predetermined position behind the objective lens 6 so as to record the reflected light on the photographic plate and block the cyclic pattern.

Operation of the foreign substance inspection apparatus of the second embodiment will be explained. A laser light beam from the laser light source 2 is converted to a parallel light beam with the collimator lens 3. Only an S polarized laser light beam 13 of the incidence plane 12 is transmitted by the polarizer 4 to irradiate only the S polarized laser light beam 13 in the incidence plane 12 to an area of the surface of the substrate 1 linearly at a relatively low angle of incidence α, about 1° to 5° by means of the cylindrical lens 5.

Only a small amount of the light beam so irradiated is reflected by the curved portion 23A of the pattern 23 on the surface of the substrate 1 to enter the objective lens 6. Since light reflected from the pattern 23 is generated according to the cyclic pattern of the pattern 23, the light becomes cyclic. As described in the explanation of the prior art, if a light beam is reflected from the pattern 23 on the surface of the substrate 1, the foreign substance inspection signal to noise ratio decreases. On the other hand, a light beam scattered by a foreign substance 24 is much greater than a light beam reflected from the pattern 23. Therefore, even if the cyclic pattern noise is cut, the intensity of a light beam reflected from the foreign substance 24 barely decreases.

Only the S polarized laser light beam 17 with respect to the detection plane 16 which is reflected from the pattern 23 and a scattered light beam from the foreign substance 24 enters the objective lens 6 and is transmitted by means of the analyzer 7. Since a cyclic pattern component caused by the curved portion 23A of the pattern 23 is eliminated from the light beam reflected by the pattern 23 and since the appropriate scattered light beam from the foreign substance 24 transmits through the analyzer 7 and the spatial filter 25, a light beam transmitting the spatial filter 25 comprises mainly the scattered light beam from the foreign substance 24. The light beam transmitted through the spatial filter 25 is focused on the line sensor 9 by means of the image formation lens 8. The S polarized laser light beam 17 in the detected plane 16 is converted photoelectrically and the detected signals are converted from analog to digital by means of the A/D converter 19. The detected analog signals converted to digital signals are compared with the threshold preset in the memory circuit 20 by the signal comparing circuit 21 to judge the existence of the foreign substance 24. Then, by moving the specimen XY moving base 22, the foreign substance inspection on the entire surface of the substrate 1 can be conducted.

According to the second embodiment, in addition to the effects of the first embodiment, since the noise caused by the reflected light beam cyclically generated by the curved portion 23A of the pattern 23 is shielded by the spatial filter 25, the noise can be minimized and the existence of the foreign substance 24 can be inspected to an even higher degree of accuracy.

(Third Embodiment)

Figure 7:
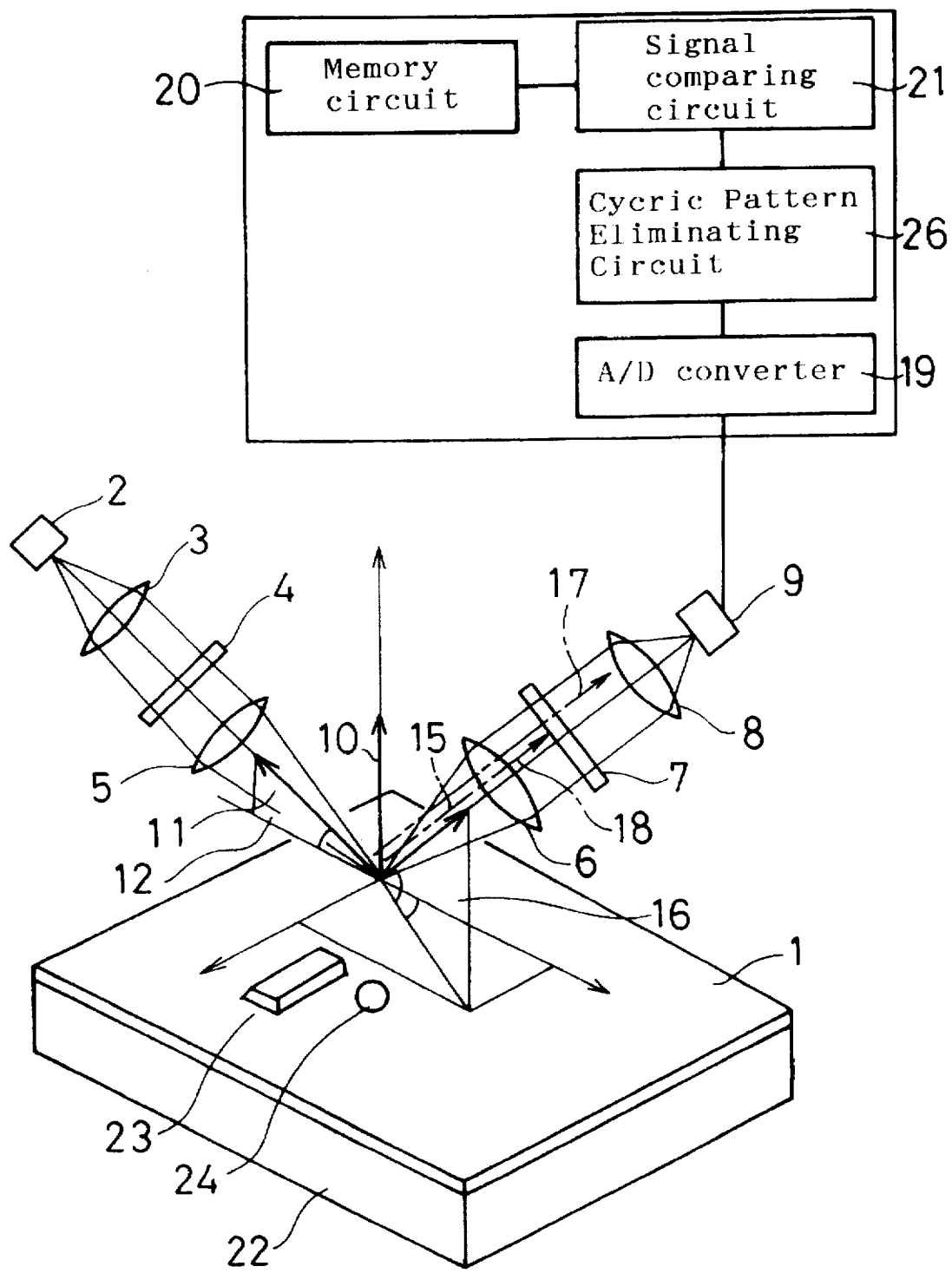
FIG. 7 is a perspective view of a foreign substance inspection apparatus of a third embodiment of the present invention.

A third embodiment of a foreign substance inspection apparatus of the present invention is illustrated in FIG. 7. Elements in FIGS. 1 and 7 bearing the same numerals are substantially the same. The apparatus of the third embodiment differs from the apparatus of the first embodiment in that the third embodiment further comprises a cyclic pattern eliminating circuit 26. The cyclic pattern eliminating circuit 26 cuts cyclic pattern noises by comparing pixels with the interval of the cyclic pattern generation.

Operation of the foreign substance inspection apparatus of the third embodiment will be explained. As in the second embodiment, a laser light beam from the laser light source 2 is converted to a parallel light beam with the collimator lens 3. Only an S polarized laser light beam 13 with respect to the incidence plane 12 is transmitted by the polarizer 4 to irradiate linearly at a comparatively low angle of incidence α, about 1° to 5° by means of the cylindrical lens 5, only the S polarized laser light beam 13 with respect to the incidence plane 12 of an area of the surface of the substrate 1 to be inspected.

Only a small amount of the light beam so irradiated is reflected by the curved portion 23A of the pattern 23 on the surface of the substrate 1 to be inspected to enter the objective lens 6. Since such light reflected from the pattern 23 is generated according to the cyclic pattern of the pattern 23, the light becomes cyclic. As described in the explanation of the prior art, if a light beam is reflected from the pattern 23 on the surface of the substrate 1 to be inspected, the foreign substance inspection signal to noise ratio decreases. On the other hand, the light beam scattered by a foreign substance 24 is much greater than the light beam reflected from the pattern 23. Therefore, even if the cyclic pattern noise is cut, the intensity of a light beam reflected from the foreign substance 24 barely decreases.

Only the S polarized laser light beam with respect to the detection plane 16 which is reflected from the pattern 23 and the light beam scattered by the foreign substance 24 enters the objective lens 6 and is transmitted by means of the analyzer 7, and focuses on the line sensor 9 by means of the image formation lens 8. The S polarized laser light beam 17 with respect to the detection plane 16 is converted photoelectrically and the detected signals are converted from analog to digital by means of the A/D converter 19. A cyclic pattern component generated by the curved portion 23A of the pattern 23 in the detected signals converted from analog to digital is eliminated by means of the cyclic pattern eliminating circuit 26. Therefore, signals outputted from the cyclic pattern eliminating circuit 26 correspond to the scattered light component from the foreign substance 24. The signals outputted from the cyclic pattern eliminating circuit 26 are compared with a threshold preset in the memory circuit 20 by the signal comparing circuit 21 to judge the existence of the foreign substance 24. Then, by moving the specimen XY moving base 22, the foreign substance inspection on the entire surface of the substrate 1 to be inspected can be conducted.

According to the third embodiment as in the second embodiment, in addition to effects of the first embodiment, since a noise caused by a reflected light beam cyclically generated by the curved portion 23A of the pattern 23 is blocked by the cyclic pattern eliminating circuit 26, noise can be minimized and the existence of a foreign substance 24 can be inspected with a high degree of accuracy.

(Fourth Embodiment)

A fourth embodiment of a foreign substance inspection apparatus of the present invention is illustrated in FIG. 8. Elements in FIG. 8 bearing the same numerals as in the first embodiment shown in FIG. 1 are substantially the same. The apparatus of the fourth embodiment differs from the apparatus of the first embodiment in that the fourth embodiment further comprises an objective lens 27 having a focal length f1, diameter D1 and the front focal plane at the back focal plane of the cylindrical lens 5, and an image formation lens 28 having a focal length f2 and diameter D2. The image formation lens 28 satisfies the below mentioned formula:

$$D2 \leq D1 - 2A + AL/f1 \quad (5)$$

wherein A denotes the inspection area determined by the detection width of the line sensor 9 and the magnification ratio of the objective lens 27 to the image formation lens 28, and L denotes the distance between the principal planes of the objective lens 27 and the image formation lens 28. Basic operation of the foreign substance inspection apparatus of the fourth embodiment is the same as the first embodiment.

Since a foreign substance inspection apparatus of the fourth embodiment further comprises an objective lens 27 and an image formation lens 28, in addition to the effects of the foreign substance inspection apparatus of the first embodiment, it has the effect of improving the off-axis signal to noise ratio. This will be explained hereinafter.

Figure 9:
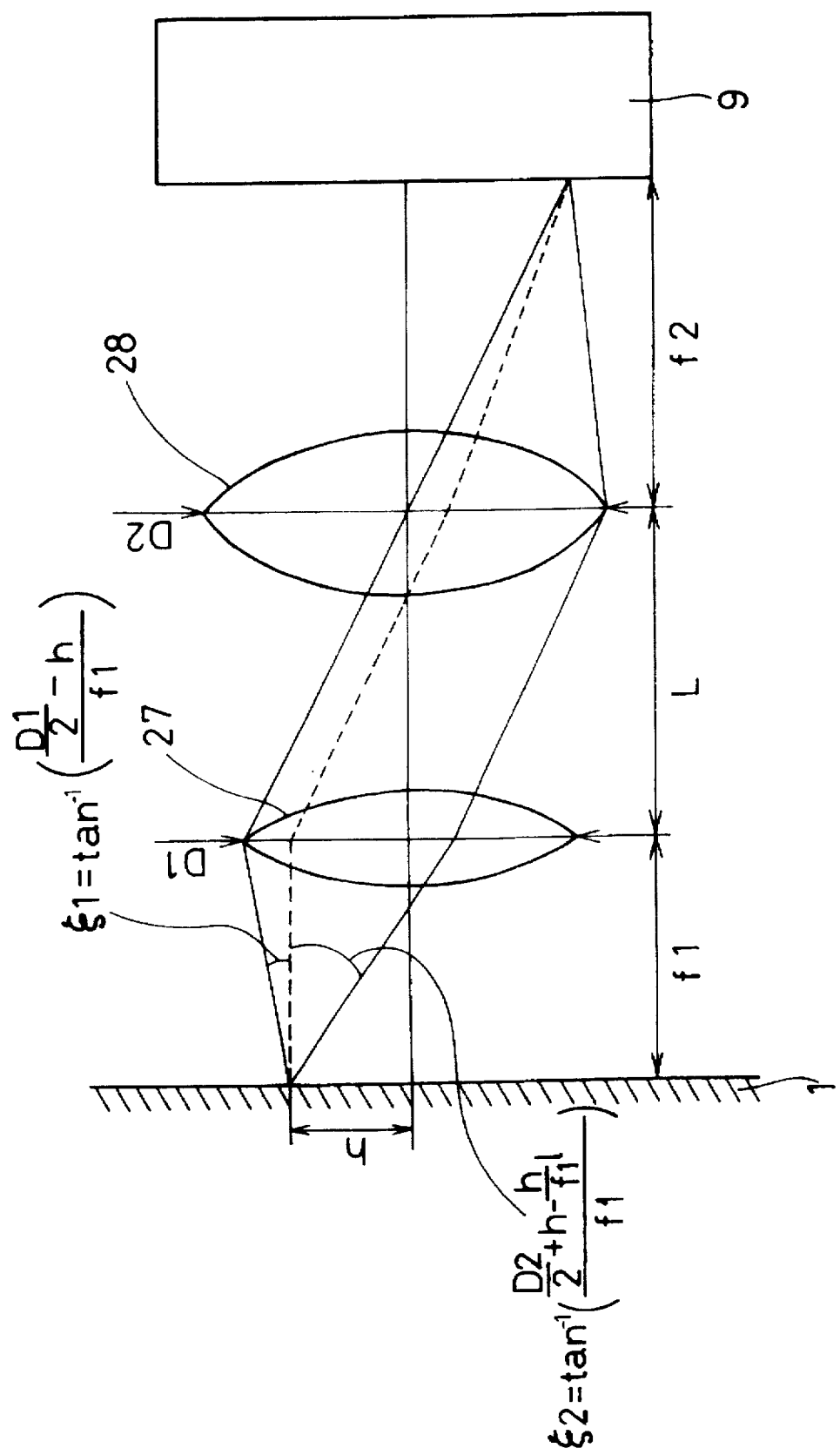
FIG. 9 is a diagram illustrating an optical system in the fourth embodiment.

FIG. 9 is a side view showing the optical axis of the detecting portion in a horizontal orientation. In FIG. 9, a light beam from the pattern 23 or the foreign substance 24 away from the optical axis by the distance h can form an image on the line sensor 9 as long as the angle $\xi 1$ is in the range defined by the below mentioned formula, $$\xi 1 = \tan^{-1}\{(D1/2 - h)/f1\} \quad (6).$$

A light beam from the pattern 23 or the foreign substance 24 away from the optical axis by the distance h can form an image on the line sensor 9 as long as the angle $\xi 2$ is in the range defined by the below mentioned formula, $$\xi 2 = \tan^{-1}\{(D2/2+h-hL/f1)/f1\} \qquad (7).$$

As shown in the above mentioned formulae (6) and (7), $\xi 1$ is determined only by the objective lens 27 while $\xi 2$ is determined by the diameter D2 of the image formation lens 28 and the distance between the principal planes L. As the distance from the optical axis widens, in other words, as the off-axis degree heightens, since the angle of a light beam accepted by the line sensor 9 decreases, the amount of a light beam from the foreign substance 24 is reduced.

On the other hand, since the light beam is reflected from the pattern 23 by direct reflection, the reflected light beam does not have a uniform distribution on the entire surface of the objective lens 27 but is concentrated on a part thereof. Therefore, even if the angle accepting a light beam becomes smaller, the intensity of the light beam reflected from the pattern 23 is barely reduced. Therefore, a problem of S/N ratio reduction occurs as the off-axis degree heightens.

In order to accept as much scattered light beam as possible from the foreign substance 24 and cope with this problem, conditions are set to have an amount of the light beam shielded by the image formation lens 28 the same as or greater than an amount of the light beam shielded by the objective lens 27. That is, with the premise of the maximum image height h=A/2 (A is the inspection area), $\xi 1 \geq \xi 2$. By substituting the relationship for the above mentioned formulae (6) and (7), the above mentioned formula (5) is obtained.

Since the diameters of the objective lens 27 and the image formation lens 28 are the same in most cases, and in order to simplify the explanation, the explanation will be given with the premise of D1=D2 hereinafter. In this case, the above mentioned formula (5) can be described as below, $$2f1 \geq L \qquad (8).$$

That is, the distance L between the principal planes is in the range of twice as much as the focal length f1. Results of computer simulation of the S/N ratio according to the change of the distance between the principal planes L and the distance from the optical axis h are shown in FIG. 10. As apparent from FIG. 10, in the case of $L \geq 2f1$, the rate of the S/N ratio reduction is small, yielding a better S/N ratio compared with the case of L> 2f1.

Accordingly, by setting the image formation lens 28 with the condition of the formula (5) or the formula (8), the rate of the off-axis signal to noise ratio reduction can be lowered.

According to the fourth embodiment, in addition to the effects of the first embodiment, by setting the image formation lens 28 with the condition of the formula (5) or the formula (8), an off-axis foreign substance 24 can be inspected with a high degree of accuracy. In combination with the second or the third embodiments, the foreign substance can be inspected with an even higher degree of accuracy.

(Fifth Embodiment)

Figure 11:
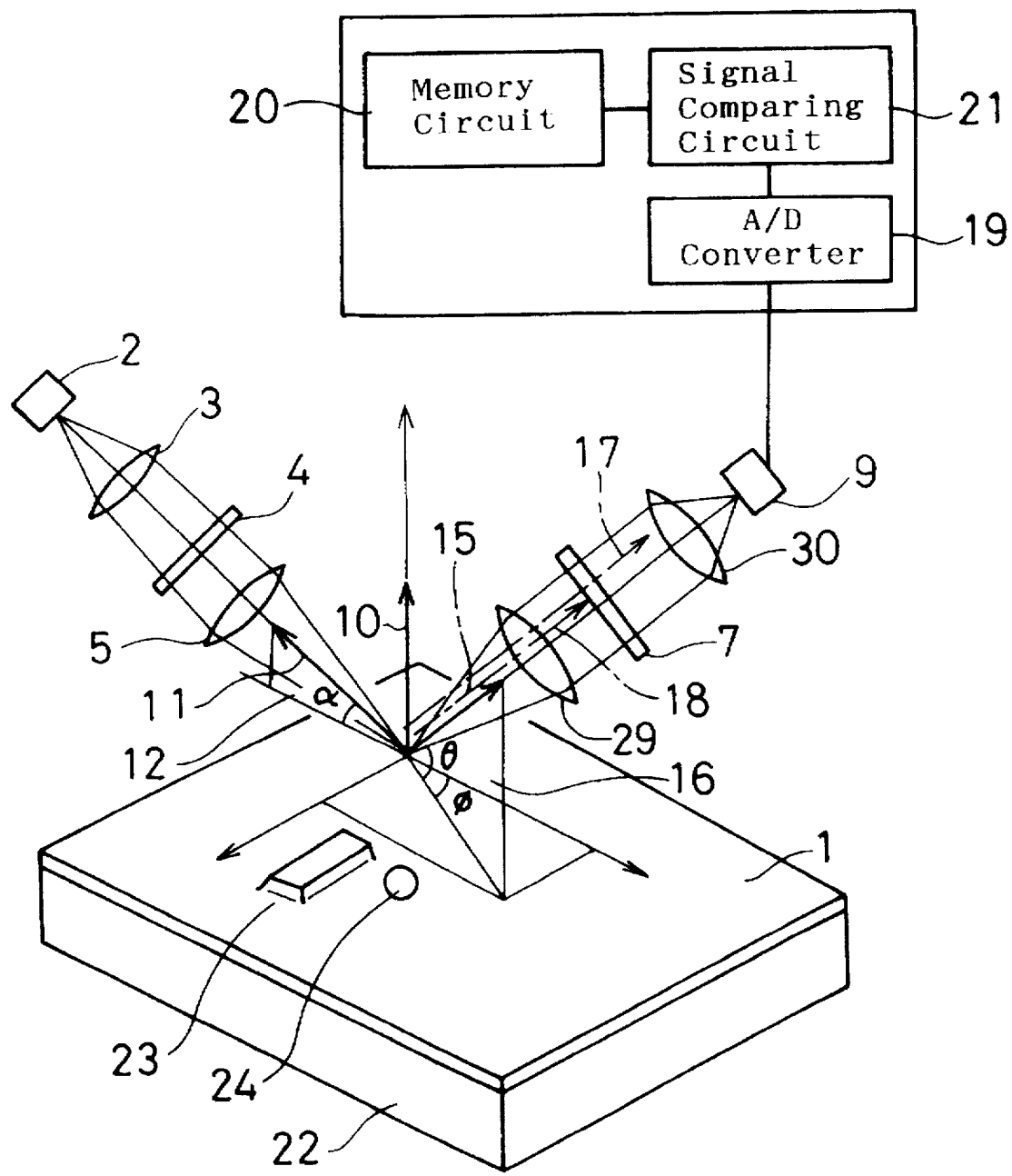
FIG. 11 is a perspective view of a foreign substance inspection apparatus of a fifth embodiment of the present invention.

A fifth embodiment of a foreign substance inspection apparatus of the present invention is illustrated in FIG. 11. Elements in FIGS. 1 and 11 bearing the same numerals are substantially the same. The apparatus of the fifth embodiment differs from the apparatus of the first embodiment in the point that both the objective lens 29 and the image formation lens 30 comprise a bi-telecentric optical system, which can be formed by placing the front focal plane of the image formation lens 30 at the back focal plane of the objective lens 29. Basic operation of the foreign substance inspection apparatus of the fifth embodiment is the same as the first embodiment.

According to the fifth embodiment, since both the objective lens 29 and the image formation lens 30 comprise a bi-telecentric optical system, even when the substrate 1 to be inspected has a wariness, the magnification ratio between the object and the image does not change. Accordingly, the size of the foreign substance 24 can be measured accurately. In combination with the second or the third Embodiments, the foreign substance can be inspected with a higher degree of accuracy.

(Sixth Embodiment)

Figure 13:
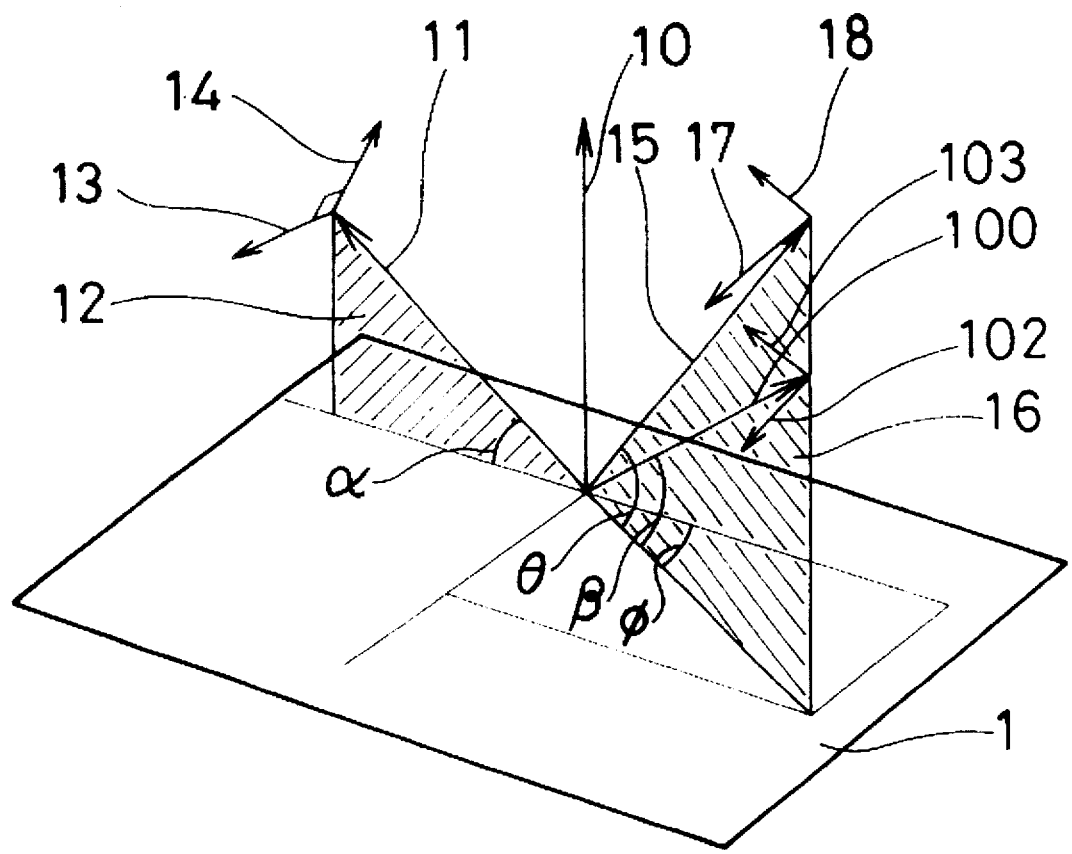
FIG. 13 is a perspective view illustrating vectors in the sixth embodiment.

A sixth embodiment of a foreign substance inspection apparatus of the present invention will be explained with reference to FIGS. 12 to 15. FIG. 12 is a perspective view of a foreign substance inspection apparatus of the sixth embodiment. FIG. 13 is a perspective view illustrating vectors in FIG. 12. Elements in the sixth embodiment illustrated in FIGS. 12 and 13 bearing the same numerals as in the first embodiment illustrated in FIGS. 1 and 2 are substantially the same. The apparatus of the sixth embodiment illustrated in FIGS. 12 and 13 differs from the apparatus of First EmbOdiment illustrated in FIGS. 1 and 2 in the point further comprising a second lighting portion.

As illustrated in FIG. 12, in the foreign substance inspection apparatus of the sixth embodiment, a first lighting portion includes a first laser light source 2, a first collimator lens 3 to convert light beams from the first laser light source 2 to parallel light beams, a first polarizer 109 and a first cylindrical lens 5 to focus the parallel light beams linearly, having the back focal plane at the surface of the substrate 1 to be inspected. A second lighting portion includes a second laser light source 104, a second collimator lens 105 to convert light beams from the second laser light source 104 to parallel light beams, a second polarizer 106, and a second cylindrical lens 107 to focus the parallel light beams linearly, having the back focal plane at the surface of the substrate 1 to be inspected. A detecting portion includes an objective lens 6 having the front focal plane at the back focal plane of the first and second cylindrical lenses 5 and 107, an analyzer 110, an image formation lens 8, and a line sensor 9 located at the focal plane of the image formation lens 8. A signal processing portion includes an analog to digital conversion circuit (A/D converter) to convert analog signals detected by the line sensor 9 to digital signals, a memory circuit 111 to store foreign substance detection thresholds and foreign substance classification thresholds preset for foreign substance inspection, a signal comparing circuit 112 for foreign substance judgment by comparing the signals outputted from the analog to digital conversion circuit 19 and a threshold stored in the memory circuit 111, and a light source controlling circuit 113 to control switching and the intensity of the first laser light source 2 and the second laser light source 104. The substrate 1 to be inspected is mounted on an XY moving base 22 and is moved two-dimensionally.

The first lighting portion and the second lighting portion are arranged to irradiate the same area of the surface of the substrate 1 to be inspected and the detecting portion picks up images of the irradiated area. In comparing the lighting portion of the first embodiment and the first lighting portion of this embodiment, they differ in the point that the first polarizer 109 of this embodiment is oriented to transmit only the P polarized laser light beam 14 in the first incidence plane 12. Further, the second polarizer 106 of this embodiment is oriented to transmit only the S polarized laser light beam 102 in the second incidence plane 101. In comparing the detecting portion of the first embodiment and the detecting portion of this embodiment, they differ in the point that the analyzer 110 of this embodiment is set to transmit only the P polarized laser light beam 18 with respect to the detection plane 16.

In FIG. 13, numeral 100 denotes the second incident orientation vector (the optical axis of the second lighting portion), 101 the second incidence plane determined by the normal vector 10 of the substrate 1 to be inspected and the second incident orientation vector 100, and 102 S polarized laser light beam in the second incidence plane 101. The S polarized laser light beam 102 has an electric vector component vibrating perpendicular to the second incidence plane 101. The P polarized laser light beam 103 in the second incidence plane has a component vibrating orthogonal to the S polarized laser light beam 102 in the second incidence plane 101. An angle of azimuth φ of the second incidence orientation vector 100 is set to be 20° to 60° and an angle of incidence β, 1° to 5°. Although the second incidence plane 101 and the detection plane 16 are identical in FIG. 13 and thus the angles of azimuth φ are the same as well, angles of azimuth can be different.

Operation of a foreign substance inspection apparatus of the sixth embodiment so formed will be explained. By the light source controlling circuit 110, the first laser light beam 2 of the first lighting portion is switched on and the second laser light source 104 is switched off. With that condition, the front scattered light beam generated by the first lighting portion is detected. In the first lighting portion, a laser light beam from the first laser light source 2 is converted to a parallel light beam by the first collimator lens 3 with respect to the first incident orientation vector 11, that is, the optical axis. By the first polarizer 109 oriented to transmit only the P polarized laser light beam 14 in the first incidence plane 12 and a linear area of the surface of the substrate 1 to be inspected is irradiated by the first cylindrical lens 5 at a comparatively low angle of incidence α, 1° to 5°. The P polarized laser light beam 14 in the first incidence plane 12 is reflected by the pattern 23 on the surface of the substrate 1 to be inspected, or scattered by the foreign substance 24.

Most of the laser light beam reflected by the pattern 23 of the substrate to be inspected does not enter the aperture of the objective lens 6 of the detecting portion having the detection orientation vector 15 as the optical axis set to have an angle of azimuth φ of 20° to 60 ° and a detecting angle θ, of 45° to 0°. On the other hand, a laser light beam scattered by the infinitesimal foreign substance 24 has an intensity distribution as illustrated in FIG. 4, and a part of the front scattered light of the laser light beam scattered by the foreign substance 24 enters the aperture of the objective lens 6 of the detecting portion. Since the front scattered light has a high absolute intensity and includes a high ratio of the P polarized laser light beam 18 in the detection plane as shown in FIG. 4, a high signal intensity can be obtained compared with a case wherein a detection orientation vector 15 is set backward or sideward.

From a light beam entering the objective lens 6, the S polarized laser light beam 17 with respect to the detection plane is shielded by the analyzer 110 to transmit only the P polarized laser light beam 18 with respect to the detection plane to be focused on the line sensor 9 by the image formation lens 8. The P polarized laser light beam 18 with respect to the detection plane is converted photoelectrically by the line sensor 9 and the detected signal is outputted to the signal processing portion. In the signal processing portion, the detected signal $S_A$ is converted by the A/D converter 19 from analog to digital and the memory circuit 111 stores the detected signal $S_A$ temporarily. p By the light source controlling circuit 113, the first laser light beam 2 in the first lighting portion is switched off and the second laser light source 104 of the second lighting portion is switched on. With that condition, the back scattered light beam generated by the second lighting portion is detected. In the second lighting portion, a laser light beam from the second laser light source 104 is converted to a parallel light beam by the second collimator lens 105 with respect to the second incident orientation vector 100, that is, the optical axis. By the second polarizer 106 oriented to transmit only the S polarized laser light beam 102 with respect to the second incidence plane and a linear area of the surface of the substrate 1 to be inspected is irradiated by the second cylindrical lens 107 at a comparatively low angle of incidence β, 1° to 5°. The S polarized laser light beam 102 with respect to the second incidence plane is reflected by the pattern 23 on the surface of the substrate 1 to be inspected, or scattered by the foreign substance 24.

When an S polarized laser light beam 102 with respect to the second incidence plane is irradiated to the pattern 23, since the polarizing orientation of the reflected light is not changed, a part of the reflected light becomes the S polarized laser light beam 17 with respect to the detection plane. After entering the aperture of the objective lens 6, the S polarized laser light beam 17 is shielded by the analyzer 11 preset to transmit only the P polarized laser light beam 18 with respect to the detection plane. On the other hand, when an S polarized laser light beam 102 with respect to the second incidence plane is irradiated to the foreign substance 24, a scattering light is generated by the foreign substance 24 to disturb the polarized component and generate a reflected light including the S polarized laser light beam 17 with respect to the detection plane and the P polarized laser light beam 18 with respect to the detection plane. From the reflected light beam after entering the objective lens 6, the S polarized laser light beam 17 with respect to the detection plane is shielded by the analyzer 110 to transmit only the P polarized laser light beam 18 with respect to the detection plane to be focused on the line sensor 9 by the image formation lens 8. The light beam focused on the line sensor 9 is converted photoelectrically by the line sensor 9 and the detected signal is outputted to the signal processing portion. In the signal processing portion, the detected signal $S_B$ is converted by the A/D converter 19 from analog to digital and the memory circuit 111 stores the detected signal $S_B$ temporarily.

Figure 18:
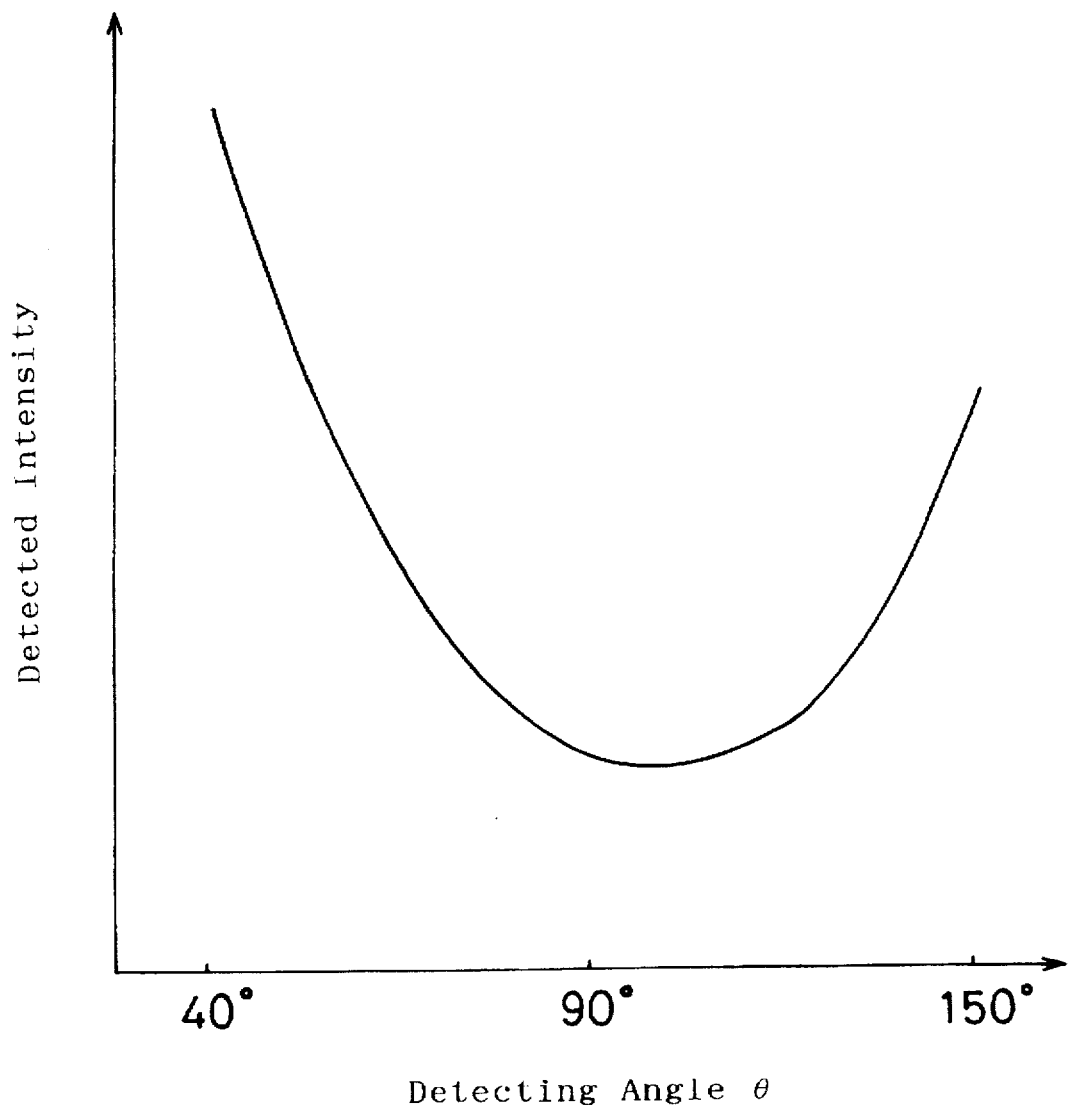
FIG. 18 is a graph illustrating a relationship between a detecting angle and a detected intensity.

By having a detecting angle θ between the second lighting portion and the detecting portion of 135° or larger to detect the back scattered light, the amount of the detected light beam from the foreign substance 24 increases as illustrated in FIG. 18. Since the light beam reflected from the pattern 23 can be reduced by using the back scattered light, the foreign substance can be detected with a high degree of accuracy.

Figure 14:
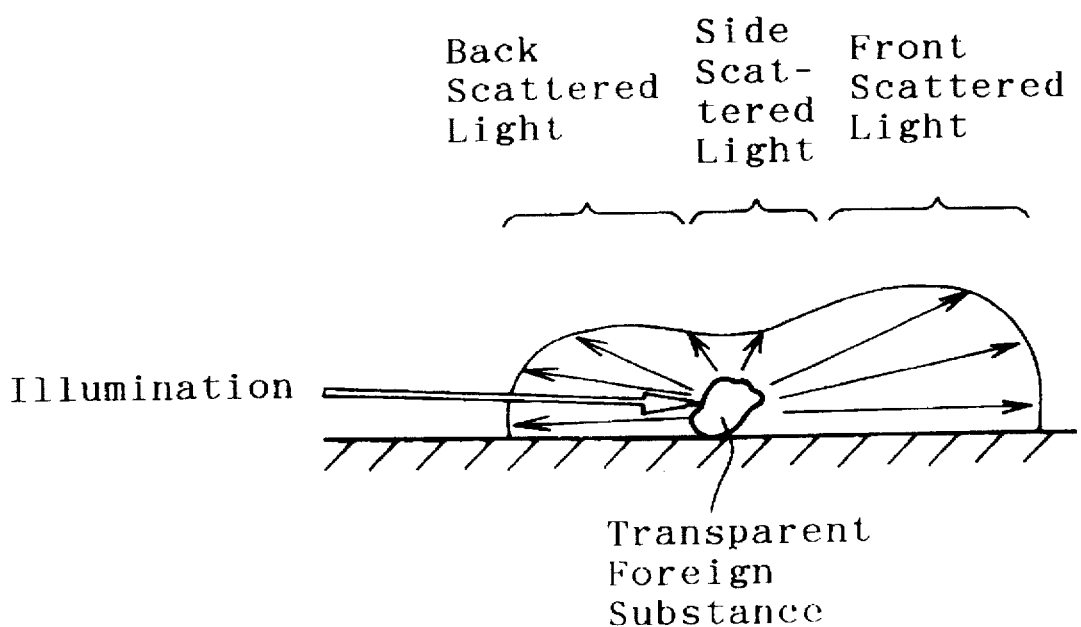
FIG. 14 is a diagram illustrating a scattered light distribution as a result of a transparent foreign substance.
Figure 15:
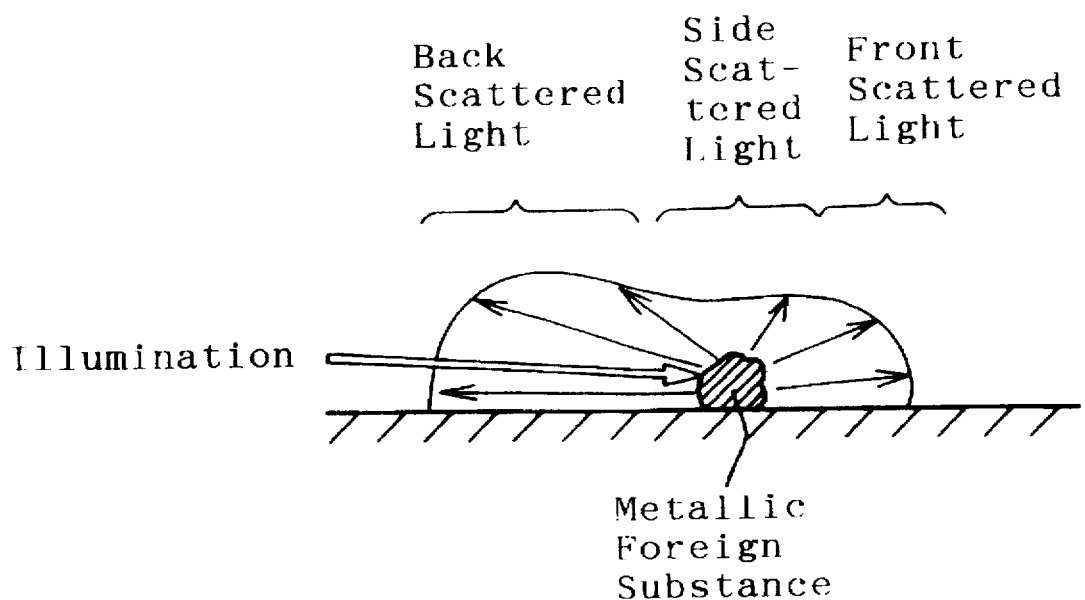
FIG. 15 is a diagram illustrating a scattered light distribution as a result of a metallic foreign substance.

The detected signal $S_A$ from the first lighting portion and the detected signal $S_B$ from the second lighting portion have characteristics mentioned below. As illustrated in FIG. 14, if the foreign substance 24 is transparent, since the light beam scattered by the foreign substance 24 is highly transmissible, the front scattered light is stronger than the back scattered light or the side scattered light in terms of the signal intensity. The front scattered light from the P polarized laser light beam 14 with respect to the first incidence plane includes the P polarized laser light beam 18 with respect to the detection plane at a high rate to have the detected signal $S_A$ with a high signal level. On the other hand, although the back scattered light from the S polarized laser light beam 102 in the second incidence plane includes the P polarized laser light beam 18 in the detection plane at a high rate, since the back scattered light has an intensity of 10% or smaller of that of the front scattered light, the detected signal $S_B$ from the back scattering light tends to be smaller than the detected signal $S_A$ from the front scattered light. On the other hand, as illustrated in FIG. 15, if the foreign substance 24 is metallic, since the scattered light from the metallic foreign substance 24 does not transmit light beams, the front scattered light becomes weaker than the back scattered light in terms of the signal intensity resulting in the detected signal $S_A$ being smaller than the detected signal $S_B$.

The signal comparing circuit 112 judges foreign substances as mentioned below by a plurality of foreign substances detecting thresholds preset in the memory circuit 111, the detected signal $S_A$ from the first lighting portion and the detected signal $S_B$ from the second lighting portion. Herein thresholds will be described as S (small size) and L (large size), foreign substance classification thresholds as CL.

When $S<S_B<L$, the foreign substance is judged to be small size. When $L<S_B$, the foreign substance is judged to be large size. When the existence of the foreign substance is detected, with the ratio of the detected front scattered signal and the detected back scattered signal $(S_A/S_B)$ as the foreign substance classification parameter, the ratio $(S_A/S_B)$ of the transparent foreign substance is large whereas the ratio $(S_A/S_B)$ of the metallic foreign substance is small. Therefore, when $CL<(S_A/S_B)$, the detected foreign substance is classified to be a metallic foreign substance.

In conventional foreign substance inspection, foreign substances are classified by methods such as visual inspection or analysis by scanning electron microscope and after setting the foreign substance generation mode, a foreign substance reduction measure is taken. In general, foreign substances attached to a substrate 1 to be inspected can be roughly divided into two categories, (1) those having light transmissivity and (2) metallic ones not having light transmissivity. Therefore by detecting the front scattered light $S_A$ from the first lighting portion and the back scattered light $S_B$ from the second lighting portion successively as in this embodiment, after detecting a foreign substance by the detected signal $S_B$ from the back scattered light, further classification of transparent foreign substances and metallic substances can be conducted by the signal intensity ratio of the detected signal $S_B$ from the back scattered light and the detected signal $S_A$ from the front scattered light. Then by moving the specimen XY moving base 22, foreign substance inspection on the entire surface of the substrate 1 to be inspected can be conducted. As a consequence, not only judgment of the size of the foreign substance from the magnitude of the detected signal, but also classification of the foreign substance, can be conducted, facilitating detection of the foreign substance generation mode thereby prompting a foreign substance reduction measure. In combination with the second embodiment to the fifth embodiment, an inspection of foreign substances with further accuracy can be conducted.

(Seventh Embodiment)

Figure 16:
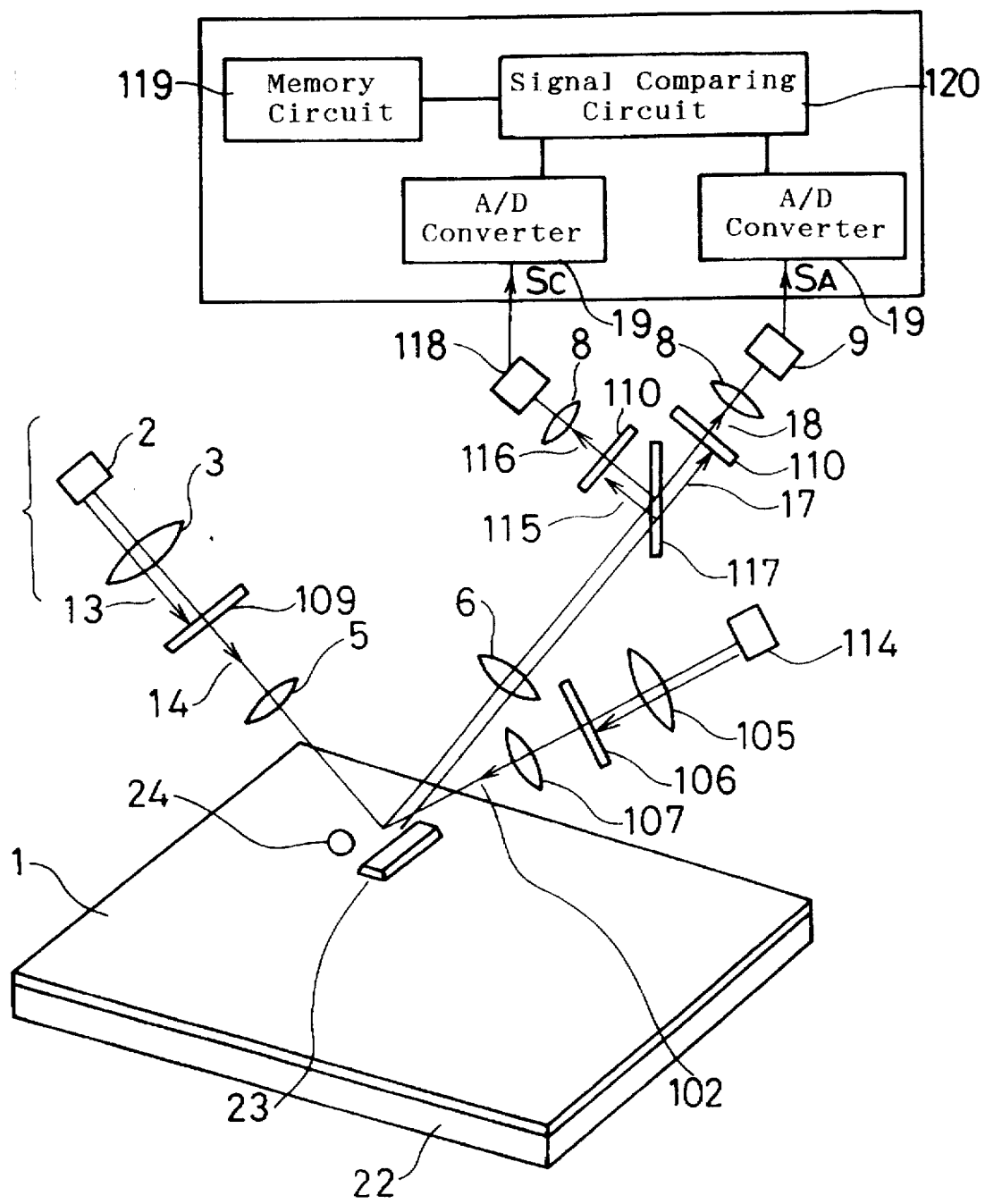
FIG. 16 is a diagram illustrating a foreign substance inspection apparatus of a seventh embodiment of the present invention.
Figure 17:
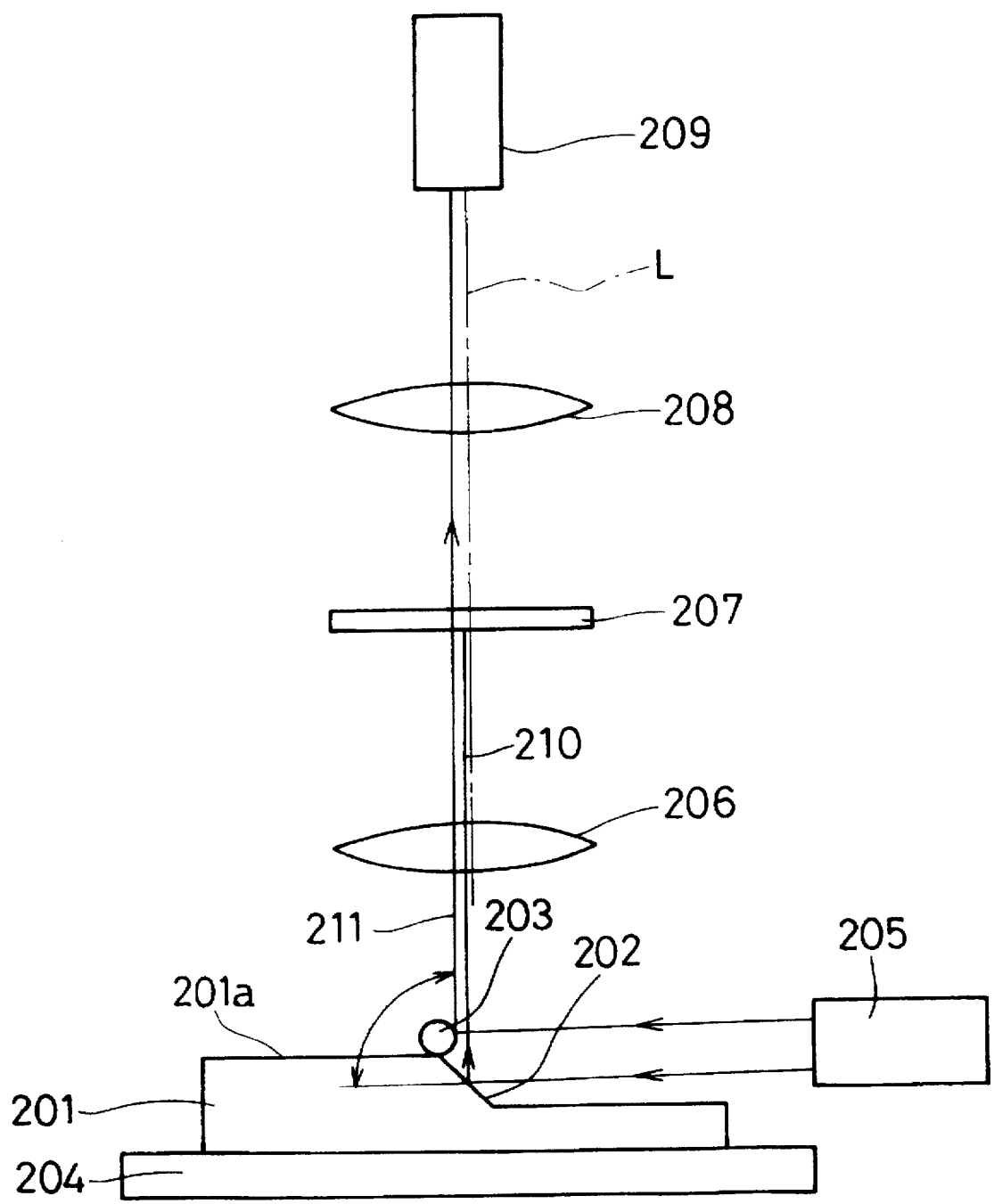
FIG. 17 is a side view illustrating a conventional foreign substance inspection apparatus.

A seventh embodiment of a foreign substance inspection apparatus of the present invention is illustrated in FIG. 16. Elements in FIG. 16 bearing the same numerals as in the sixth embodiment illustrated in FIGS. 12 and 13 are substantially the same.

As illustrated in FIG. 16, in the foreign substance inspection apparatus of the seventh embodiment, a first lighting portion includes a first laser light source 2, a first collimator lens 3 to convert light beams from the first laser light source 2 to parallel light beams, a first polarizer 109 and a first cylindrical lens 5 to focus the parallel light beams linearly, having the back focal plane at the surface of the substrate 1 to be inspected. A second lighting portion includes a second laser light source 114, a second collimator lens 105 to convert light beams from the second laser light source 114 to parallel light beams, a second polarizer 106, and a second cylindrical lens 107 to focus the parallel light beams linearly, having the back focal plane at the surface of the substrate 1 to be inspected. A detecting portion includes an objective lens 6 having the front focal plane at the back focal plane of the first and second cylindrical lenses 5 and 107, a dichroic mirror to transmit laser light beams with a wavelength λ1 and reflect laser light beams with a wavelength λ2, an analyzer 110 oriented so as to transmit only the P polarized laser light beam with wavelengths in the detection plane 16, an image formation lens 8 to focus an image of the substrate 1 to be inspected on line sensors, and a first line sensor 9 to detect a wavelength of λ1 and a second line sensor 118 to detect a wavelength of λ2. A signal processing portion includes an analog to digital conversion circuit (A/D converter) 19 to convert analog signals detected by the first line sensor 9 and the second line sensor 118 to digital signals, a memory circuit 119 to store foreign substance detection thresholds and foreign substance classification thresholds preset for foreign substance inspection and a signal comparing circuit 120 for foreign substance judgment by comparing the signals outputted from the analog to digital conversion circuit 19 and a threshold stored in the memory circuit 119. The substrate 1 to be inspected is placed on an XY moving base 22 and is moved two-dimensionally. The wavelength λ2 of the second laser light source 114 of the second lighting portion and the wavelength λ1 of the first laser light source 2 of the first lighting portion are different. The detecting portion has a detection orientation vector 15 as the optical axis with an angle of azimuth φ of 20° to 60° and the detecting angle θ of 45° to 0°.

In FIG. 16, numeral 17 denotes the S polarized laser light beam having a wavelength λ1 of the detection plane 16, 115 the S polarized laser light beam having a wavelength λ2 of the detection plane 16, 18 the P polarized laser light beam having the wavelength λ1 of the detection plane 16, and 116 the P polarized laser light beam having the wavelength λ2 of the detection plane 16. Although the second incidence plane 101 and the detection plane 16 are identical in FIG. 16 and thus the angles of azimuth φ are the same as well, angles of azimuth can be different. As in the sixth embodiment, the first lighting portion and the second lighting portion are set to irradiate the same area on the surface of the substrate 1 to be inspected, and the detecting portion picks up images in the irradiated area.

Operation of a foreign substance inspection apparatus of the seventh embodiment so formed will be explained from the detection of the front scattered light beam generated by the first lighting portion with the wavelength λ1. In the first lighting portion having the incidence orientation vector 11 as the optical axis, a laser light beam from the first laser light source 2 having the wavelength λ1 is converted to a parallel light beam by the first collimator lens 3 with respect to the first incidence orientation vector 11, that is, the optical axis. By the first polarizer 109 oriented to transmit only the P polarized laser light beam 14 in the first incidence plane 12, a linear area of the surface of the substrate 1 is irradiated by the first cylindrical lens 5 at a comparatively low angle of incidence α, 1° to 5°. The P polarized laser light beam 14 in the first incidence plane 12 is reflected by the pattern 23 on the surface of the substrate 1, or scattered by the foreign substance 24.

Most of the laser light beam reflected by the pattern 23 of the substrate 1 to be inspected does not enter the aperture of the objective lens 6 of the detecting portion having the detection orientation vector 15 as the optical axis set to have an angle of azimuth $\phi$ of 20° to 60° and a detecting angle $\theta$ of 45° to 0°. On the other hand, a laser light beam scattered by the infinitesimal foreign substance 24 has an intensity distribution as illustrated in FIG. 4, and a part of the front scattered light beam having the wavelength of $\lambda 1$ of the laser light beam scattered by the foreign substance 24 enters the aperture of the objective lens 6 of the detecting portion. From a front scattered light entering the objective lens 6 having the wavelength of $\lambda 1$, after transmitting the dichroic mirror 117, the S polarized laser light beam having the wavelength of $\lambda 1$ 17 with respect to the detection plane is blocked by the analyzer 110 to transmit only the P polarized laser light beam having the wavelength of $\lambda 2$ 18 with respect to the detection plane and focued on the first line sensor 9 by the image formation lens 8. The P polarized laser light beam 18 in the detection plane is converted photoelectrically by the line sensor 9 and the detected signal is outputted to the signal processing portion. In the signal processing portion, the detected signal $S_A$ is converted by the analog to digital conversion circuit 19 from analog to digital and the memory circuit 119 stores the detected signal $S_A$ temporarily.

Detection of the back scattered light from the second lighting portion with the wavelength $\lambda 2$ will be explained. In the second lighting portion having the second incidence orientation vector 100 as the optical axis, a laser light beam from the second laser light source 114 having the wavelength $\lambda 2$ is converted to a parallel light beam by the second collimator lens 105 with respect to the second incidence orientation vector 100, that is, the optical axis. By the second polarizer 106 oriented to transmit only the S polarized laser light beam having the wavelength of $\lambda 2$ 102 in the second incidence plane and a linear area of the surface of the substrate 1 to be inspected is irradiated by the second cylindrical lens 107 at a comparatively low angle of incidence $\beta$, 1° to 5°. The S polarized laser light beam having the wavelength of $\lambda 2$ 102 in the second incidence plane is reflected by the pattern 23 on the surface of the substrate 1 to be inspected, or scattered by the foreign substance 24. When an S polarized laser light beam 102 with respect to the second incidence plane is irradiated to the pattern 23, since the polarizing orientation of the reflected light is maintained, a part of the reflected light becomes the S polarized laser light beam having the wavelength of $\lambda 2$ 115 with respect to the detection plane. After entering the aperture of the objective lens 6 and being reflected by the dichroic mirror 117, the S polarized laser light beam 115 is shielded by the analyzer 110 preset to transmit only the P polarized laser light beam with respect to the detection plane. On the other hand, when an S polarized laser light beam 102 with respect to the second incidence plane is irradiated to the foreign substance 24, a scattered light is generated by the foreign substance 24 to disturb the polarized component and generate a reflected light including the S polarized laser light beam having the wavelength of $\lambda 2$ 115 with respect to the detection plane and the P polarized laser light beam having the wavelength of $\lambda 2$ 116 with respect to the detection plane. From the reflected light beam after entering the objective lens 6 and being reflected by the dichroic mirror 117, the S polarized laser light beam 115 in the detection plane is shielded by the analyzer 110 to transmit only the P polarized laser light beam 116 in the detection plane to be focused on the second line sensor 118 by the image formation lens 8. The light beam focused on the line sensor 118 is converted photoelectrically by the line sensor 118 and the detected signal is outputted to the signal processing portion. In the signal processing portion, the detected signal $S_C$ is converted by the analog to digital conversion circuit 19 from analog to digital and the memory circuit 119 stores the detected signal $S_C$ temporarily.

The detected signal $S_A$ from the first lighting portion and the detected signal $S_C$ from the second lighting portion have characteristics mentioned below. As illustrated in FIG. 14, if the foreign substance 24 is transparent, the front scattered light is stronger than the back scattered light or the side scattered light in terms of the signal intensity. The front scattered light beam from the P polarized laser light beam 14 with respect to the first incidence plane includes the P polarized laser light beam 18 with respect to the detection plane at a high rate to have the detected signal $S_A$ with a high signal level. On the other hand, although the back scattered light from the S polarized laser light beam 102 with respect to the second incidence plane includes the P polarized laser light beam 18 with respect to the detection plane at a high rate, since the back scattered light has an intensity of 10% or smaller of that of the front scattered light, the detected signal $S_C$ from the back scattered light tends to be smaller than the detected signal $S_A$ from the front scattered light. On the other hand, as illustrated in FIG. 15, if the foreign substance 24 is metallic, the front scattered light becomes weaker than the back scattered light in terms of the signal intensity to have the detected signal $S_A$ smaller than a detected signal $S_C$.

The signal comparing circuit 120 judges foreign substances as mentioned below by a plurality of foreign substances detecting thresholds preset in the memory circuit 119, the detected signal $S_A$ from the first lighting portion and the detected signal $S_C$ from the second lighting portion. Herein thresholds will be described as S (small size) and L (large size), foreign substance classification thresholds as CL.

When $S<S_C<L$, the foreign substance is judged to be small size. When $L<S_C$, the foreign substance is judged to be large size. When the existence of the foreign substance is detected, with the ratio of the detected front scattered signal and the detected back scattered signal $(S_A/S_C)$ as the foreign substance classification parameter, the ratio $(S_A/S_C)$ of the transparent foreign substance is large whereas the ratio $(S_A/S_C)$ of the metallic foreign substance is small. Therefore, when $CL<(S_A/S_C)$, the detected foreign substance is classified to be a metallic foreign substance. By using the new foreign substance classification parameter, not only the detection of the foreign substance as in conventional methods, but also classification of the foreign substance can be conducted. Further, since in the method of the seventh embodiment using two kinds of wavelengths, the front scattered light from the first lighting portion and the back scattered light from the second lighting portion are separated at the detecting portion, the detected signal $S_A$ by the front scattered light and the detected signal $S_C$ by the back scattered light are detected simultaneously, the foreign substance is detected by the detected signal $S_C$ by the back scattered light, and further a metallic foreign substance can be classified at the time of detection by the signal intensity ratio of the detected signal $S_C$ by the back scattered light and the detected signal $S_A$ by the front scattered light, then unlike the sixth embodiment, detection can be conducted in continuous lighting with stability without switching of lighting portions. Unlike the sixth embodiment, where the front scattered light and the back scattered light are detected successively and the specimen needs to be kept stationary, since scattered lights are detected simultaneously in this embodiment, the specimen XY moving base 22 can be inspected while continuously moving. In combination with the second to fifth Embodiments, foreign substance inspection can be conducted with a further degree of accuracy.

Although a line sensor is used in the detecting portion and an XY moving base is used as the specimen moving method in the above mentioned embodiments, a photoelectrical conversion element such as a photodiode or a photomultiplier can be used in the detecting portion and a specimen moving method including rotation can be used as well. Although a cylindrical lens is used in the lighting portion, a linear irradiating light can be achieved by means of a slit.

As this invention can be embodied in several forms without departing from the spirit of essential characteristics thereof, the present embodiments are therefore illustrative and not restrictive, since the scope of the invention is defined by the appended claims rather than by the description preceding them, and all changes that fall within the metes and bounds of the claims, or equivalents of such metes and bounds are therefore intended to embraced by the claims.

What is claimed is:

1. A foreign substance inspection apparatus comprising:
   a lighting portion located so as to have an optical axis inclined to a surface to be inspected having thereon an object to be inspected, irradiating with an S polarized light beam with respect to the surface; and
   a detecting portion having an optical axis located in a position set by rotating the optical axis of the lighting portion by 120° to 160° with the point of intersection of the optical axis of the lighting portion and the surface to be inspected as the center of rotation so as to have an angle made with the surface to be inspected of 45° or smaller, to detect an area to which the light beam is irradiated by the lighting portion by detecting an S polarized component in a scattered component from foreign substances existing on the surface to be inspected and converting the S polarized component photoelectrically.

2. The foreign substance inspection apparatus according to claim 1, further comprising a signal processing means to eliminate a cyclic pattern of the object to be inspected from signals outputted from the detecting portion.

3. The foreign substance inspection apparatus according to claim 2, wherein the signal processing portion further comprises a cyclic pattern eliminating circuit to cut a cyclic pattern noise.

4. The foreign substance inspection apparatus according to claim 1, wherein the detecting portion includes a telecentric optical system.

5. The foreign substance inspection apparatus according to claim 1, wherein the lighting portion comprises a laser light source, a collimator lens to convert light beams from the laser light source to parallel light beams, a polarizer and a cylindrical lens to focus the parallel light beams linearly having the back focal plane at the surface to be inspected, and wherein the detecting portion comprises an objective lens having the front focal plane at the back focal plane of the cylindrical lens, an analyzer, an image formation lens and a line sensor located at the focal plane of the image formation lens.

6. The foreign substance inspection apparatus according to claim 5, wherein the detecting portion comprises at least an optical system including an objective lens having a focal length of f and an aperture diameter of D1, and an image formation lens having the principal plane with a distance L from the principal plane of the objective lens and preset to have the aperture diameter D2 satisfying the below mentioned formula:

$$D2 \geq D1 - 2A + (AL/f)$$

wherein A denotes the width of the area to be inspected.

7. The foreign substance inspection apparatus according to claim 1, wherein the detecting portion comprises an analog to digital conversion circuit to convert an analog signal outputted from the line sensor to a digital signal, a memory circuit to store a predetermined threshold to detect foreign substances, and a signal processing portion including a signal comparing circuit to compare the signal outputted from the analog to digital conversion circuit and a threshold stored in the memory circuit to inspect foreign substances.

8. The foreign substance inspection apparatus according to claim 5, further comprising a spatial filter located between the objective lens and the image formation lens of the detecting portion to eliminate a cyclic pattern of the object to be inspected.

9. The foreign substance inspection apparatus according to claim 8, wherein the spatial filter is prepared by making and recording a Fourier transform image of a cyclic pattern data of the surface to be inspected of the object to be inspected on a photographic plate so as to block the cyclic pattern.

10. The foreign substance inspection apparatus according to claim 8, wherein the spatial filter is prepared by irradiating a cyclic pattern of the surface to be inspected of the object to be inspected and recording reflected light on a photographic plate located at a predetermined position behind the objective lens so as to block the cyclic pattern.

11. A foreign substance inspection apparatus comprising:
   a first lighting portion located so as to have a first optical axis inclined to a surface to be inspected having thereon an object to be inspected, irradiating with a P polarized light beam with respect to the surface;
   a second lighting portion having a second optical axis located in a position set by rotating the first optical axis of the first lighting portion by 90° or larger with a point of intersection of the first optical axis and the surface to be inspected as a center of rotation, irradiating with an S polarized light beam with respect to the surface;
   a detecting portion to detect an area to which the light beams are irradiated from the first lighting portion and the second lighting portion by successively detecting a P polarized component in a front scattered component generated from a foreign substance existing on the surface to be inspected by the first lighting portion and a P polarized component in a back scattered component generated from a foreign substance by the second lighting portion and converting the P polarized components photoelectrically, having a third optical axis located in a position set by rotating the first optical axis by 120° to 160° at the point of intersection of the first optical axis and the surface to be inspected as a center of rotation so as to have an angle made with the surface to be inspected by 45° or smaller; and
   a signal processing portion to detect foreign substances based on signals outputted from the detecting portion and to classify light transmissivities of the foreign substances by comparing intensities of the front scattered component and the back scattered component.

12. The foreign substance inspection apparatus according to claim 11, further comprising a signal processing means to eliminate a cyclic pattern of the object to be inspected from signals outputted from the detecting portion.

13. The foreign substance inspection apparatus according to claim 12, wherein the signal processing portion further comprises a cyclic pattern eliminating circuit to cut a cyclic pattern noise.

14. The foreign substance inspection apparatus according to claim 11, wherein the detecting portion includes a telecentric optical system.

15. The foreign substance inspection apparatus according to claim 11, wherein the first lighting portion comprises a first laser light source, a first collimator lens to convert light beams from the first laser light source to parallel light beams, a first polarizer and a first cylindrical lens to focus the parallel light beams linearly, and having a first back focal plane at the surface to be inspected, wherein the second lighting portion comprises a second laser light source, a second collimator lens to convert light beams from the second laser light source to parallel light beams, a second polarizer and a second cylindrical lens to focus the parallel light beams linearly and having a second back focal plane at the surface to be inspected;

wherein the detecting portion comprises an objective lens having a front focal plane at the back focal planes of the first and second cylindrical lenses, an analyzer, an image formation lens and a line sensor located at the focal plane of the image formation lens; and wherein the signal processing portion comprises an analog to digital conversion circuit to convert analog signals outputted from the line sensor to digital signals, a memory circuit to store foreign substance detection thresholds and foreign substance classification thresholds preset for foreign substance inspection, a signal comparing circuit for foreign substance judgment by comparing the signals outputted from the analog to digital conversion circuit and the thresholds stored in the memory circuit and a light source controlling circuit to control switching and intensity of the first and second laser light sources.

16. The foreign substance inspection apparatus according to claim 15, wherein the first lighting portion includes a first polarizer oriented to transmit only the P polarized component of a light beam irradiated from the first lighting portion, the second lighting portion includes a second polarizer oriented to transmit only the S polarized component of a light beam irradiated from the second lighting portion, and the detecting portion includes an analyzer set to transmit only the P polarized component of a light beam entering the detecting portion.

17. The foreign substance inspection apparatus according to claim 15, wherein the detecting portion comprises at least an optical system including an objective lens having a focal length of f and an aperture diameter of D1, and an image formation lens having the principal plane with a distance L from the principal plane of the objective lens and preset to have the aperture diameter D2 satisfying the below mentioned formula:

$$D2 \geq D1 - 2A + (AL/f)$$

wherein A denotes the width of the area to be inspected.

18. The foreign substance inspection apparatus according to claim 11, wherein the first lighting portion and the second lighting portion are set to irradiate the same area of the surface of the object to be inspected and the detecting portion detects images of the area.

19. The foreign substance inspection apparatus according to claim 15, further comprising a spatial filter located between the objective lens and the image formation lens of the detecting portion to eliminate a cyclic pattern of the object to be inspected.

20. The foreign substance inspection apparatus according to claim 19, wherein the spatial filter is prepared by making and recording a Fourier transform image of a cyclic pattern data of the surface to be inspected of the object to be inspected on a photographic plate so as to block the cyclic pattern.

21. The foreign substance inspection apparatus according to claim 19, wherein the spatial filter is prepared by irradiating a cyclic pattern of the surface to be inspected of the object to be inspected and recording reflected light on a photographic plate located at a predetermined position behind the objective lens so as to block the cyclic pattern.

22. A foreign substance inspection apparatus comprising:

a first lighting portion located so as to have a first optical axis inclined to the surface to be inspected having thereon an object to be inspected and irradiating with a P polarized light beam with respect to the surface;

a second lighting portion having a second optical axis located in a position set by rotating the first optical axis by 90° or larger with a point of intersection of the first optical axis and the surface to be inspected as a center of rotation, irradiating with an S polarized light beam with respect to the surface having a wavelength different from that of the first lighting portion;

a detecting portion to detect an area to which the light beams are irradiated from the first lighting portion and the second lighting portion by separating a P polarized component in a front scattered component generated from a foreign substance existing on the surface to be inspected by the first lighting portion and the P polarized component in a back scattered component generated from the foreign substance by the second lighting portion with a wavelength separating device, and detecting them simultaneously to be converted photoelectrically, having a third optical axis located in a position set by rotating the first optical axis by 120° to 160° at the point of intersection of the first optical axis and the surface to be inspected as the center of rotation so as to have an angle made with the surface to be inspected of 45°; and a signal processing portion to detect foreign substances based on signals outputted from the detecting portion and to classify light transmissivities of the foreign substances by comparing intensities of a front scattered component and a back scattered component.

23. The foreign substance inspection apparatus according to claim 22, further comprising a signal processing means to eliminate a cyclic pattern of the object to be inspected from signals outputted from the detecting portion.

24. The foreign substance inspection apparatus according to claim 23, wherein the signal processing portion further comprises a cyclic pattern eliminating circuit to cut a cyclic pattern noise.

25. The foreign substance inspection apparatus according to claim 22, wherein the detecting portion includes a telecentric optical system.

26. The foreign substance inspection apparatus according to claim 22, wherein the first lighting portion comprises a first laser light source to emit a laser light beam having a wavelength of $\lambda 1$, a first collimator lens to convert light beams from the first laser light source to parallel light beams, a first polarizer and a first cylindrical lens to focus the parallel light beams linearly and having a first back focal plane at the surface of the substrate to be inspected;

the second lighting portion comprises a second laser light source to emit a laser light beam having a wavelength of $\lambda 2$, a second collimator lens to convert light beams from the second laser light source to parallel light beams, a second polarizer and a second cylindrical lens to focus the parallel light beams linearly, and having a second back focal plane at the surface of the substrate to be inspected;

the detecting portion comprises an objective lens having a front focal plane at the back focal planes of the first and second cylindrical lenses, a dichroic mirror to transmit a laser light having wavelength of $\lambda 1$ and to reflect a laser light having wavelength of $\lambda 2$, an analyzer oriented so as to transmit only the P polarized component of wavelengths $\lambda 1$ and $\lambda 2$ in the detection plane, an image formation lens to focus images in the surface to be inspected on a line sensor, a first line sensor to detect laser light having wavelength of $\lambda 1$, and a second line sensor to detect laser beam having wavelength of $\lambda 2$; and the signal processing portion comprises an analog to digital conversion circuit to convert analog signals detected by the first line sensor and the second line sensor to digital signals, a memory circuit to store foreign substance detection thresholds and foreign substance classification thresholds preset for foreign substance inspection, and a signal comparing circuit for foreign substance judgment by comparing the signals outputted from the analog to digital conversion circuit and the thresholds stored in the memory circuit.

27. The foreign substance inspection apparatus according to claim 26, wherein the detecting portion comprises at least an optical system including an objective lens having a focal length of f and an aperture diameter of D1, and an image formation lens having the principal plane with a distance L from the principal plane of the objective lens and preset to have the aperture diameter D2 satisfying the below mentioned formula:

$$D2 \geq D1 - 2A + (AL/f)$$

wherein A denotes the width of the area to be inspected.

28. The foreign substance inspection apparatus according to claim 26, further comprising a spatial filter located between the objective lens and the image formation lens of the detecting portion to eliminate a cyclic pattern of the object to be inspected.

29. The foreign substance inspection apparatus according to claim 28, wherein the spatial filter is prepared by making and recording a Fourier transform image of a cyclic pattern data of the surface to be inspected of the object to be inspected on a photographic plate so as to block the cyclic pattern.

30. The foreign substance inspection apparatus according to claim 28, wherein the spatial filter is prepared by irradiating a cyclic pattern of the surface to be inspected of the object to be inspected and recording reflected light on a photographic plate located at a predetermined position behind the objective lens so as to block the cyclic pattern.

* * * * *

UNITED STATES PATENT AND TRADEMARK OFFICE
CERTIFICATE OF CORRECTION

PATENT NO. : 5,717,485

DATED : FEBRUARY 10, 1998

INVENTOR(S): ITO ET AL.

It is certified that error appears in the above-identified patent and that said Letters Patent is hereby corrected as shown below:

Col. 3, line 36: "plano" should read -- plane --

Col. 10, line 67: insert "." after "32°"

Col. 14, line 41: "$D2\leqq$" should read -- $D2\geqq$ --

Col. 15, line 44: "$L\geqq$" should read -- $L\leqq$ --

Col. 18, line 1: delete "p" and insert new paragraph at "By the"

Signed and Sealed this

Tenth Day of November 1998

*Attest:*

BRUCE LEHMAN

*Attesting Officer*     *Commissioner of Patents and Trademarks*